United States Patent [19]

Protiva et al.

[11] 4,431,808
[45] Feb. 14, 1984

[54] TRICYCLIC COMPOUNDS

[75] Inventors: Miroslav Protiva; Karel Sindelář; Antonin Dlabač; Jiřina Metysova, all of Prague, Czechoslovakia

[73] Assignee: SPOFA, spojene podniky pro zdravotnickou vyrobu, Prague, Czechoslovakia

[21] Appl. No.: 356,474

[22] Filed: Mar. 9, 1982

[30] Foreign Application Priority Data

Mar. 13, 1981 [CS] Czechoslovakia .................... 1841-81

[51] Int. Cl.³ .................. C07D 411/04; C07D 409/04; C07D 407/04
[52] U.S. Cl. ................................... 546/197; 549/349; 549/10; 549/11; 424/267
[58] Field of Search ........................... 549/349, 10, 11; 546/197

[56] References Cited

U.S. PATENT DOCUMENTS

| | | | |
|---|---|---|---|
| 3,100,207 | 8/1963 | Zirkle | 549/354 |
| 3,501,483 | 3/1970 | Howell et al. | 548/531 |
| 3,639,423 | 2/1972 | Winter et al. | 549/354 |

FOREIGN PATENT DOCUMENTS 2480283 10/1981 France .

*Primary Examiner*—Norma S. Milestone

[57] ABSTRACT

A technique is described for the preparation of a wide variety of basic derivatives of linearly condensed tricyclic systems formed by two external benzene nuclei and a 7-membered central ring having 2 chalcogen atoms as hetero atoms.

Derivatives of 11H-dibenzo(b,e)-1,4-dioxepin are obtained when the chalcogens are both oxygen atoms; derivatives of 11H-dibenzo(b,f)-1,4-dithiepin are obtained when the chalcogens are both sulfur atoms; derivatives of 6H-dibenz(b,e)-1,4-oxathiepin and 11H-dibenz(b,f)-1,4-oxathiepin are obtained with combinations of sulfur and oxygen atoms as chalcogens.

12 Claims, No Drawings

TRICYCLIC COMPOUNDS

This invention relates to basic derivatives of tricyclic compounds of the formula

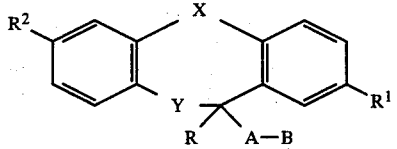

wherein
X and Y are selected from the group consisting of oxygen, sulfur, SO and $SO_2$, X and Y being identical or different,
R represents hydrogen or a methyl group,
$R^1$ represents hydrogen, a halogen atom, an alkyl, alkoxyl or alkylthio group 1-3 carbon atoms,
$R^2$ represents hydrogen of fluorine,
A represents a saturated hydrocarbon chain of 1-3 carbon atoms, and
B is selected from the group consisting of $N(CH_3)_2$, $NHCH_3$ and a piperidine (1-piperidyl) group.

Alternatively, the fragment A—B may be selected from among (a)

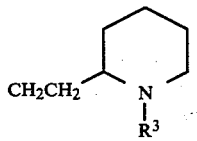

(b)

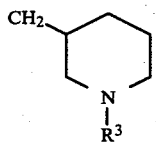

and (c)

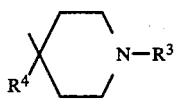

wherein
$R^3$ represents hydrogen, methyl, hydroxyalkyl of 2-5 carbon atoms and acyloxyalkyl of a maximum of 15 carbon atoms, and
$R^4$ represents hydrogen or a hydroxyl group.

The invention also relates to the N oxides and salts of said compounds with pharmaceutically acceptable acids and method for the preparation thereof.

The compounds of formula (I) are derived from the tricyclic skeletons set forth below, the chemistry of which has almost been unknown heretofore:

(a) 11H-dibenzo(b,e)-1,4-dioxepin of the formula II

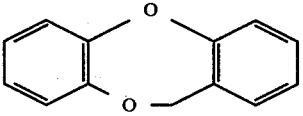

(b) 11H-dibenz(b,f)-1,4-oxathiepin of the formula III

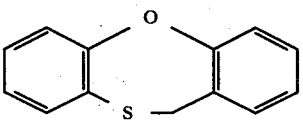

(c) 6H-dibenz(b,e)-1,4-oxathiepin of the formula IV

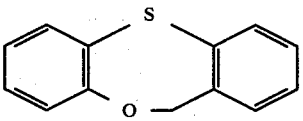

(d) 11H-dibenzo(b,e)-1,4-dithiepin of the formula V

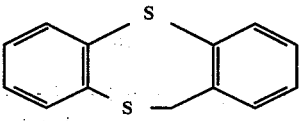

A synthesis of the compound of formula II, which is designated as depsidane, was described in two papers (Inubushi Y., J. Pharm. Soc. Japan 72, 1223, 1952; Tomita M. et al., Yakugaku Zasshi 80, 358, 1960; Chem. Abstr. 47, 12 408, 1953; 54, 18 432, 1960). The corresponding 11-oxo compounds, i.e. the lactone depsidone, is the basic substance of an important group of lichen metabolites designated in general as depsidones. The basic depsidone was synthesized by several groups (Tomita M. et al., J. Pharm. Soc. Japan 64, 173, 1944, Chem. Abstr. 45, 6173, 1951; Noyce D. S., Weldon J. W., J. Amer. Chem. Soc. 74, 401, 1952; Neelakantan S. et al., Curr. Sci. 33, 365, 1964) and the synthesis of more complicated lichen depsidones was described in a series of communications (Cresp T. M. et al., Aust. J. Chem. 28, 2417, 1975; Djura P. et al., J. Chem. Soc., Perkin Trans. I 1976, 147. The synthesis of compounds of formulae III and IV has been described in a preliminary form without more detailed experimental data (Sindelar K., Holubek J., Protiva M., 6th Smyp. Chem. Heterocycl. Compounds, Brno 1978; Abstracts of papers, p. 95; Heterocycles 9, 1498, 1978). Additionally, the synthesis of a substituted 6-oxo derivative of compound IV, i.e. 2-methyl-8-nitro-6-oxo-dibenz (b,e)-1,4-oxathiepen (Galbraith F., Smiles S., J. Chem. Soc. 1935, 1234; Chem. Zentralbl. 1935, II, 3498) has been described. Finally, the system of compound V is known only in the form of the 1,2,3,4,4a, 11a-hexahydro derivative which was obtained as a minor product of photolysis of 2,3-benzo-1,5-dithiaspiro (5.5) undecane in cyclo-hexane (Kohrman R. E., Berchtold G. A., J. Org. Chem. 36, 3971, 1971). None of the compounds mentioned interferes with the object of this invention and with the exception of compound III, whose synthesis has been described by the authors of this invention in a preliminary form, none of the noted compounds is of use as a starting product in the synthesis of compounds of this invention.

The compounds of this invention are of interest from a therapeutic standpoint because they evidence psychotropic activity in conjunction with acceptable (very mild) levels of toxicity. Based upon the construction of the molecule, that is, the character of $R^1$ and $R^2$ and the character of hydrocarbon member A, which connects the skeleton with the amino group, the described compounds are antidepressants, tranquilizers or neuroleptic agents. It has been determined that when $R^1$ and $R^2$ are both hydrogen, A is a saturated hydrocarbon chain of 1-3 carbon atoms and B is either dimethylamino or methylamino, the resultant compounds evidence antireserpine activity and are suitable for use as antidepressants. Studies have revealed that in certain instances, the intensity of their antireserpine activity exceeds that of the conventional antidepressants, i.e., imipramine and amitriptyline. In the event that $R^1$ is not hydrogen and the A-B residue is 1-methyl-4-piperidyl or 1-(hydroxy-alkyl)-4-piperidyl, the resultant compounds are neuroleptics evidencing a high level of central depressant, cataleptic and antiapomorphine activity. If $R^2$ is fluorine, the neuroleptic efficacy is even higher and evidences prolongation after oral administration. The intermediate types of compound in accordance with the invention evidence a mild or significant central depressant activity and their use as tranquilizers is indicated.

All of the noted compounds may be administered orally. However, the esters of the neuroleptically active aminoalcohols, included in this invention, such as esters of higher fatty acids, may be administered by injection intramuscularly as solutions in vegetable oils. Under these circumstances the the compounds are considered depot neuroleptics and the therapeutic effect of a single dose of 10-25 mg of the substance may last as long as several weeks.

Accordingly, it is apparent that the pharmacological activity of the compounds of the invention indicates their use in treating mental depression, psychoses of the schizophrenic area and of neurotic states.

In order to demonstrate the pharmacological properties of compounds of the invention, studies of several of these compounds were made after oral administration with the noted doses calculated for the bases. The testing procedure employed conventional prior art techniques described in the literature.

Acute toxicity was determined by evaluation of groups of 10 femal mice. The rate of perishing was evaluated for 7 days following oral administration and results are expressed as medium lethal doses $LD_{50}$ in mg/kg.

The incoordinating activity as a criterion of the central depressant action was determined in mice by the rotarod test (Metysova J. et al., Arzneim-Forsch. 13, 1039, 1963). The medium effective doses eliciting ataxia ($ED_{50}$) were estimated in the interval of the optimum effect of the compound tested.

The inhibition of the locomotor activity of mice (also as a criterion of the central depressant action) was determined by the photo-cell method (Dews P. B., Brit. J. Pharacol. 8, 46, 1953). The dose was estimated which decreases the average control value of the spontaneous locomotor activity by 50% ($D_{50}$).

The inhibition effect on the motility of mice was further followed by the observation test by Ther (Ther L., Deut. Apoth.-Ztg. 93, 292, 1953). The doses given ($D_{50}$) bring about an effect which corresponds with 50% of the average control value.

The potentiation of the hypnotic effect of thiopental in mice was used as a further non-specific criterion of the central depressant action of the compounds (Metysova J. Metys J., Int.J. Neuropharmacol. 4, 111, 1965). Doses are given which prolong the sleeping time after a standard dose of thiopental.

The hypothermic effect in mice is also typical for substances having central depressant activity and for neuroleptics (Metysova J., Metys J., reference given above).

Antagonism of ptosis in mice elicited with reserpine is an indication of a possible antidepressant effect (Metysova J., Metys J., reference given above). Doses are given which antagonize the reserpine ptosis with statistical significance.

Antagonism of the hypothermic effect of reserpine in mice is a further indication of an antidepressant effect (Metysova J., Metys J., reference given above). The administered doses are given and the number of °C. by which the body temperature is elevated in comparison with the reserpine control group is evaluated.

Antagonization of the ulcerogenic effect of reserpine in rats was also used for the identification of a possible antidepressant action (Metysova J., Metys J., reference given above). Doses are given which significantly antagonize the ulcerogenic effects of reserpine.

The cataleptic effect was determined in female rates, using the method of Boissier and Simon (Therapie 18,1257, 1963). Medium effective doses ($ED_{50}$) bringing about catalepsy in 50% of the animals in the experiment are given.

The antiapomorphine effect (a further indication of the neuroleptic action) was studied in male rats, using the test of Janssen et al. (Arzneim.-Forsch. 10, 1003, 1960; 17, 841, 1967. Doses $D_{50}$ are given which inhibit the "chewing" (stereotypsies) and "agitation", elicited by apomorphine, to 50% of the apomorphine control group.

The antiapomorphine activity of the depot neuroleptics was evaluated in dogs using the method of Janssen and Miemegeers (Arzneim.-Forsch. 9, 765, 1959): it was verified in weekly intervals whether the blockade of the vomiting (elicited by a subcutaneous administration of apomorphine hydrochloride), is still maintained.

Other properties, e.g. hypotensive, adrenologytic, spasmolytic, antihistamine, local anesthetic, were estimated using conventional techniques.

For comparative purposes, results obtained with several standards in the most significant tests are given:

Acute toxicity, $LD_{50}$ values in mg/kg: chlorpromazine, 198; clorothepin, 78; imipramine, 370; amitriptyline, 225, dosulepin, 320.

Incoordinating effect (ataxia), $ED_{50}$ values in mg/kg: chlorpromazine, 8.2; clorothepin, 2.2.

Inhibition of locomotor activity according to Dews, $D_{50}$ values in mg/kg: chlorpromazine, 4.8; clorothepin, 1.1.

Inhibition of motility according to Ther; $D_{50}$ values in mg/kg: chlorpromazine, 4.8.

Potentiation of the hypnotic effect of thiopental, the threshold is given: chlorpromazine, 2.5.

Hypothermic effect, the threshold dose (in mg/kg) lowering the body temperature is given: chlorpromazine, 5.0.

Antagonism of the hypothermic effect of reserpine: an oral dose of 10 mg/kg imipramine elevates the body temperature by 2.97° C. in comparison with the reserpine control group; a dose of 10 mg/kg of amitriptyline elevates the body temperature by 2.51° C.

Antagonism of the ulcerogenic effect of reserpine; doses ED in mg/kg having a significant effect: imipramine, 25; dosulepin, 50.

Cataleptic effect, doses $ED_{50}$ in mg/kg: chlorpromazine, 16.0; clorothepin, 4.3.

Antiapomorphine effect in rates, doses $D_{50}$ in mg/kg (a) for chewing and (b) for agitation: chlorpromazine, (a) 69, (b) 38; clorothepin, (a) 10.8.

It is necessary to mention that the neuroleptic agents, used as standards (chlorpromazine, clorothepin), have effects which do not show prolongation, i.e. they practically disappear within 24 hours in all the tests described.

Pharmacological data for individual substances of the present invention are set forth below:

11-(3-Dimethylaminopropyl)-11H-dibenzo(b,e-1,4-dioxepin (tested as the hydrogen maleate, compound 14062): Toxicity, $LD_{50}=500$ mg/kg; incoordinating effect, $ED_{50}=21$ mg/kg. The substance is a mild tranquilizer.

6-(3-Dimethylaminopropyl)-6H-dibenz(b,e)-1,4-oxathiepin (tested as a hydrogen maleate), compound 14017: Toxicity, $LD_{50}$ between 200 and 500 mg/kg (the dose of 200 mg/kg is non-toxic, the dose of 500 mg/kg is lethal for 80% of the animals). On intravenous administration, the $LD_{50}=40$ mg/kg. Incoordinating effect, $ED_{50}=46.8$ mg/kg. Inhibition of motility, $D_{50}=4$ mg/kg. Antireserpine activity toward hypothermia: a dose of 10 mg/kg elevates the temperature in comparison with the reserpine control group by 2.42° C., which is effective to the result obtained with amitriptyline. Potentiation of thiopental, with a dose of 5 mg/kg i.v. prolongs the sleeping time by 100% in comparison with the control group. The hypotensive effect in normotensive rates; a dose of 0.5 mg/kg i.v. lowers the blood pressure by 10% for a short time period. The α-adrenolytic effect; a dose of 2 mg/kg i.v. inhibits the adrenaline pressor reaction in rats by 50%. The spasmolytic (parasympatholytic effect in vitro; in a concentration of 5 μg/ml. The compound inhibits the acetylcholine contractions of an isolated rat duodenum by 50%. Spasmolytic (myotropic) effect in vitro; in a concentration of 5 μg/ml. The compound inhibits the barium chloride contractions of an isolated rat duodenum by 50%. The antihistamine effect; a dose of 0.5–1.0 mg/kg s.c. protects 50% of the treated guinea pigs from the lethal effect of a dose of 5 mg/kg histamine, administered intrajugularly. The substance is an antidepressant with a mild sedative activity and several common neurovegetative effects of moderate intensity.

6-(3-Piperidinopropyl)-6H-dibenz(b,e)-1,4-oxathiepin (tested in the form of the hydrogen maleate, compound 14061): Toxicity, $LD_{50}=320$ mg/kg. After i.v. administration, $LD_{50}=22.5$ mg/kg. The incoordinating effect, $ED_{50}=25$ mg/kg. Inhibition of the locomotor activity (Dews), $D_{50}=10$–30 mg/kg. The antireserpine activity, ptosis, ED=100 mg/kg. The substance is a mild tranquilizer with indication of antidepressant activity.

6-(1-Methyl-3-piperidylmethyl)-6H-dibenz(b,e)-1,4-oxathiepin (tested in the form of the hydrogen oxalate, compound 14060): Toxicity, $LD_{50}$ is higher than 500 mg/kg (this dose is lethal for 30% of the treated mice). Incoordinating effect, $ED_{50}=32$ mg/kg. In a dose of 100 mg/kg the compound shows an indication of inhibition of the ulcerogenic effect of reserpine. The substance is a mild tranquilizer with indication of antidepressant activity.

6-(1-Methyl-4-piperidyl)-6H-dibenz(b,e)-1,4-oxathiepin (tested in the form of the hydrogen maleate, compound 14018): Toxicity, $LD_{50}$ between 200 (a non-toxic dose) and 500 mg/kg $LD_{100}$). Incoordinating effect, $ED_{50}=4.2$ mg/kg. Inhibition of motility (Ther $D_{50}=3.5$ mg/kg. Hypothermic effect, a dose of 5 mg/kg lowers the temperature by 2.31° C.; the same doses of chlorpromazine or perphenazine lower the temperature 1.92° C., or 2.86° C., respectively. A dose of 10 mg/kg. lowers the body temperature by 3.75° C.; the same dose of chlorpromazine or perphenazine lowers the temperature 3.86° C., or 3.85° C., respectively. Catalepsy, $ED_{50}$ between 50 (catalepsy in 15% of the treated aminals) and 100 mg/kg $ED_{60}$); the effect is masked by a deep central depression. With a dose of 50 mg/kg the compound potentiates the cataleptic action of perphenazine. The substance is evaluated as a very potent transquilizer with a weak cataleptic component of activity.

8-Chloro-6-(1-methyl-4-piperidyl)-6H-dibenz(b,c)-1,4-ozathiepin (tested in the form of the hydrogen maleate, compound 14107). Toxicity, $LD_{50}=108$ mg/kg. Incoordinating effect, $ED_{50}=2.0$ mg/kg; cataleptic effect, $ED_{50}=4.2$ mg/kg. The substance is neuroleptic which is significantly more potent than chlorpromazine; by the intensity of its effect and by toxicity it resembles clorothepin.

8-Chloro-6-methyl-6-(3-dimethylaminopropyl)-6H-dibenz(b,e)-1,4-oxathiepin (tested in the form of the hydrogen oxalate, compound 14059): Toxicity, $LD_{50}=556$ mg/kg. Incoordinating effect, $ED_{50}=39$ mg/kg. Inhibition of the locomotor activity (Dews), $D_{50}=100$ mg/kg. The compound is a mild tranquilizer.

8-Chloro-6-methyl-6-(1-methyl-4-piperidyl)-6H-dibenz (b,e)-1,4-oxathiepin (tested in the form of the hydrogen oxalate, compound 14085): Incoordinating effect, $ED_{50}=75$ mg/kg. Catalepsy, a dose of 100 mg/kg brought about catalepsy in 20% of the treated animals. The substance is a mild tranquilizer, almost free of cataleptic action.

8-Methoxy-6-(1-methyl-4-piperidyl)-6H-dibenz(b,e)-1,4-oxathiepin (tested in thc form of the hydrogen maleate, compound 14.087). Toxicity, $LD_{50}=98$ mg/kg. Incoordinating effect, $ED_{50}=.92$ mg/kg; cataleptic effect, $ED_{50}=3.6$ mg/kg. The substance is a highly potent neuroleptic with a higher intensity of effect than observed for chlorpromazine or clorothepin.

8-Trifluoromethyl-6-(1-methyl-4-piperidyl)-6H-dibenz(b,e)-1,4-oxathiepin (tested as the hydrogen oxalate, compound 14088): Toxicity, $LD_{50}=115$ mg/kg. Incoordinating effect, $ED_{50}=2.6$ mg/kg. Cataleptic effect, $ED_{50}=1.8$ mg/kg. The substance is a highly potent neuroleptic agent surpassing the activity of chlorpromazine and clorothepin.

2-Fluoro-8-chloro-6-(1-methyl-4-piperidyl)-6H-dibenz(b,e)-1,4-oxathiepin (tested in the form of the hydrogen maleate, compound 14135): Toxicity, $LD_{50}=184$ mg/kg. The incoordination effect appears with some latency and is strongly protracted; within 2 hours after administration, the $ED_{50}=0.9$ mg/kg, in 3 hours $ED_{50}=0.3$ mg/kg (maximum effect). After 24 hours, $ED_{50}=1.4$ mg/kg, after 48 hours 3.2 mg/kg, after 72 hours 5.0 mg/kg. After 96 hours ataxia appeared in 20% of the treated mice. The cataleptic effect, $ED_{50}=1.7$ mg/kg. The antiapomorphine activity in rats $D_{50}=1.14$ mg/kg (inhibition of the chewing) and 1.06 mg/kg (inhibition of the agitation). The substance is an extremely active neuroleptic agent surpassing chlorpromazine in the test of antiapomorphine activity by almost 100 times; the depressant effects show a high degree of protraction.

2-Fluoro-8-methyl-6-1(1-methyl-4-piperidyl)-6H-dibenz (b,e)-1,4-oxathiepin (tested in the form of hydrogen maleate, compound 14105): Toxicity, $LD_{50}=164$ mg/kg.

Upon intravenous administration, $LD_{50}=60$ mg/kg. The incoordinating effect appears with latency and is significantly protracted; within 2 hours after the administration, $ED_{50}=0.77$ mg/kg; the optimum effect appeared in the 4th hour, $ED_{50}=0.46$ mg/kg, in 24 hours $ED_{50}=2.3$ mg/kg, in 48 hours 3.6 mg/kg. The cataleptic effect, $ED_{50}=3.0$ mg/kg. The antiapomorphine activity in rats, $D_{50}=2.9$ mg/kg (inhibition of the chewing), 3.5 mg/kg (inhibition of the agitation). The compound exhibited an analgetic effect in the Haffner test at doses of 1–5 mg/kg. i.v., at concentrations of 0.1–0.5% a local anesthetic effect in the test of conreal anesthesia was evident, it also evidenced a significant α-adrenolytic efficacy (a dose of 0.1 mg/kg i.v. lowered the adrenaline pressor reaction in rats by 50%), in a concentration of 1 μg/ml it inhibited the acetylcholine contraction of an isolated rat duodenum by 50%, similary in concentrations of 1–10 μg/ml it inhibited barium chloride contractions. In doses of 1–5 mg/kg i.v. it lowered the body temperature of rats (measured rectally) by 1° C. (hypothermic activity). In doses of 0.1–1.0 mg/kg s.c. it protected 50% of treated guineapigs from a lethal dose of histamine (antihistamine activity). In doses of 0.1–1.0 mg/kg it prolonged the thiopental sleeping time in mice by 100% in comparison with the thiopental control group. It also had a significant antiamphetamine action; doses of 0.01–0.1 mg/kg protected 100% of treated mice from the lethal effect of a standard dose of amphetamine. The substance is a highly potent neuroleptic with a higher intensity of effect than shown by chlorpromazine or clorothepin, with an accompanying high antiapomorphine activity and an important protraction of depressant effect.

2-Fluoro-8-(trifluoromethylthio)-6-(1-methyl-4-piperidy)-6H-dibenz(b,e)-1,4-oxathiepin (tested in the form of the hydrogen maleate, compound 14716): Toxicity, $LD_{50}=338$ mg/kg. The incoordinating effect (as in the preceding cases) is delayed and is significantly protracted; within 2 hours after administration, $ED_{50}=3.0$ mg/kg, the optimum effect appears within 5 hours after administration, $ED_{50}=1.8$ mg/kg, in 24 hours $ED_{50}=6.0$ mg/kg, in 48 hours a dose of 10 mg/kg produces ataxia in 30% of the treated mice in 72 hours in 10% of the mice. Similarly (as with the preceding compound), this substance is a highly potent neuroleptic with a strongly protracted depressant effect.

11-(2-Dimethylaminoethyl)-11H=dibenz(b,e)-1,4-dithiepin (tested in the form of hydrogen oxalate, compound 14019): Toxicity, $LD_{50}$ between 200 (a non-toxic dose) and 500 mg/kg (lethal for 60% of the treated animals). The incoordinating effect, $ED_{50}=143$ mg/kg. Inhibition of motility (Ther), $D_{50}=17$ mg/kg. It strongly antagonized the body temperature by 4.22° C. in comparison with the reserpine control group. It was significantly more effective than imipramine or amitriptyline. The substance may be characterized as an antidepressant with a very mild central depressant activity.

11-(3-Dimethylaminopropyl)-11H-dibenz(b,e)-1,4-dithiepin (tested in the form of the hydrogen oxalate, compound 14020): Toxicity, $LD_{50}$ between 200 (a nontoxic dose) and 500 mg/kg. Inhibition of motility (Ther), $D_{50}=20$ mg/kg. This compound intensively antagonized the hypothermic action of reserpine; a dose of 10 mg/kg elevated the body temperature by 3.8° C. in comparison with the reserpine control group, such being more effective than imipramine or amitriptyline. The substance is an antidepressant with a low central depressant activity.

11-(2-Dimethylaminoethyl)-11H-dibenz(b,f)-1,4-oxathiepin (tested in the form of the hydrogen oxalate, compound 14091): Toxicity, $LD_{50}=227$ mg/kg. The incoordinating effect, $ED_{50}=57.5$ mg/kg. The substance is a mild tranquilizer.

11-(Dimethylaminopropyl)-11H-dibenz(b,f)-1,4-oxathiepin (tested in the form of the hydrogen oxalate, compound 14090): Toxicity, $LD_{50}=373$ mg/kg. Incoordinating effect, $ED_{50}=61.9$ mg/kg. Inhibition of the locomotor activity (Dews) is apparent starting with a dose of 50 mg/kg. The substance is a mild tranquilizer.

2-Chloro-11-(3-dimethylaminopropyl)-11H-dibenz(b,f)-1,4-oxathiepin (tested in the form of the hydrogen oxalate, compound 14016). Toxicity, $LD_{50}$ between 200 (a non-toxic dose) and 500 mg/kg (lethal for 80% of treated animals). The incoordinating effect, $ED_{50}=84.9$ mg/kg. Inhibition of motility (Ther), $D_{50}=10$ mg/kg. The antireserpine effect toward hypothermia; a dose of 10 mg/kg elevated the body temperature by 1.42° C. in comparison with the reserpine control group. The substance is an antidepressant with mild central depressant activity.

2-Chloro-11-(2-dimethylaminoethyl)-11H-dibenz(b,f)-1,4-oxatiepin 10,10-dioxide (tested in the form of the hydrochloride, compound 14111): Incoordinating effect, a dose of 100 mg/kg produces ataxia in 60% of the treated mice within 2 hours after administration. The substance is a very mild tranquilizer.

2-Chloro-11-(3-piperidionopropyl)-11H-dibenz(b,f)-1,4-oxathiepin 10,10-dioxide (tested in the form of the hydrochloride, compound 14120): Incoordinating effect, $ED_{50}=75$ mg/kg. With a dose of 100 mg/kg it evidenced mild antagonism toward the reserpine ptosis in mice. The substance is a mild tranquilizer with an indication of antidepressant activity.

2-Chloro-11-(1-methyl-4-piperidyl)-11H-dibenz(b,f)-1,4-oxathiepin (tested in the form of the hydrogen maleate, compound 14103): Toxicity, $LD_{50}=299$ mg/kg. The incoordinating effect is clearly protracted; within 2 hours after administration $ED_{50}=14$ mg/kg, after 24 hours a dose of 25 mg/kg produces ataxia in 30% of the mice. The cataleptic effect, $ED_{50}=41$ mg/kg. The substance is a mild neuroleptic with a reduced cataleptic component of activity.

2-Trifluoromethyl-11-(1-methyl-4-piperidyl)-11H-dibenz(b,f)-1,4-oxathiepin (tested in the form of the hydrogen oxalate monohydrate, compound 14086): Toxicity, $LD_{50}=384$ mg/kg. Incoordinating effect, $ED_{50}=12$ mg/kg. Inhibition of the locomotor activity (Dews), $D_{50}=5.7$ mg/kg. The cataleptic effect, $ED_{50}=4.7$ mg/kg. The antiapomorphine activity in rats, $D_{50}=1.7$ mg/kg (for the inhibition of the apomorphine chewing), 1.4 mg/kg (for the inhibition of the apomorphine agitation). The substance is a very active neuroleptic with a relatively low central depressant activity.

11-(2-Methylaminoethyl)-11H-dibenz(b,f)-1,4-oxathiepin (tested in the form of the hydrogen oxalate, compound 14092): Toxicity, $LD_{50}=250$ mg/kg. Incoordinating effect, $ED_{50}=60.2$ mg/kg. Inhibition of motility (Ther), $D_{50}=50$ mg/kg. Antireserpine effect towards the ptosis, ED-10 mg/kg. Antireserpine effect towards the ulcerogenic action, ED-50 mg/kg. The substance is an antidepressant with a significant intensity of effect with a mild central depressant component.

11-(3-Methylaminopropyl)-11H-dibenz(b,f)-1,4-oxathiepin (tested in the form of the hydrogen oxalate, compound 14093): Toxicity, $LD_{50}$-284 mg/kg. On i.v. administration $LD_{50}=30$ mg/kg. The incoordinating effect, $ED_{50}=79.5$ mg/kg. The antireserpine effect towards the ptosis, ED-150 mg/kg; on i.p. administration ED-6 mg/kg. The substance is an antidepressant with a mild central depressant component of action.

8-Methoxy-6-/1-(2-hydroxyethyl)-4-piperidyl/-6H-dibenz(b,e)-1,4-oxathiepin (tested in the form of the hydrogen fumarate, compound 14106): Incoordinating effect, $ED_{50}=2.8$ mg/kg., after 24 hours 10 mg/kg. The cataleptic effect, $ED_{50}=8.0$ mg/kg. The substance is a neuroleptic agent which is more active than chlorpromazine.

8-Methoxy-6-/1(4-hydroxypentyl)-4-piperidyl/-6H-dibenz(b,e)-1,4-oxathiepin (tested in the form of the hydrogen fumarate, compound 14108): The incoordinating effect, $ED_{50}=10$ mg/kg 2 hours after administration), after 24 hours 19.5 mg/kg. The cataleptic effect, $ED_{50}=5.6$ mg/kg. The antiapomorphine activity in rats, $D_{50}=3.1$ mg/kg for the inhibition of chewing), 2.5 mg/kg (for the inhibition of agitation). The substance is a significantly active neuroleptic with a relatively low central depressant component of action.

2-Fluoro-8-chloro-6-/1-(2-decanoyloxyethyl)-4-piperidyl/-6H-dibenz(b,e)-1,4-oxathiepin (tested as base, compound 14717, and also in the form of a hydrogen maleate, compound 14719): Toxicity, $LD_{50}=425$ mg/kg (orally). The antiapomorphine activity in rats after the i.m. administration of a solution in Miglyol; a single administration of a dose of 25 mg/kg produced an antiapomorphine effect which lasted for 3 days, a dose of 50 mg/kg had an effect lasting 8 days. In the test of antiapomorphine activity in dogs, a dose of 5 mg/kg. i.m. blocked the apomorphine emesis for 2 weeks after administration, in the 3rd week the effect disappeared. The substance evidences properties of a depot neuroleptic of the fluphenazine decanoate type.

2-Chloro-11-(1-methyl-4-hydroxy-4-piperidyl)-11H-dibenz(b,f)-1,4-oxathiepin (tested in the form of the hydrogen maleate, compound 14104): Incoordinating effect, $ED_{50}=56$ mg/kg. The substance is a very mild tranquilizer which is free of the cataleptic effect.

11-(Dimethylaminomethyl)-11H-dibenz(b,f)-1,4-oxathiepin (tested in the form of the hydrogen oxalate, compound 14089): Incoordinating effect, $ED_{50}=23.8$ mg/kg. Antireserpine action toward the ptosis, ED-10 mg/kg. The substance is an antidepressant with a mild central depressant action.

As noted above, encompassed within the subject invention are salts of the compound designated by formula I with pharmaceutically acceptable organic and inorganic acids. Compounds which have been found to be of particular interest are the hydrochlorides and acid salts with dicarbonylic aliphatic acids (oxalic, maleic and fumaric which are moderately in water and suitable for preparing a drug for oral administration. These compounds are also more suitable for carrying out pharmacological testing than the free bases. The free bases (such as the highly lipophilic esters) are suitable for intramuscular administration in the form of a solution in oil.

An integral part of the present invention resides in the method for preparing compounds within the scope of formula I and salts thereof as well as oxidation products thereof (N-oxides). The following techniques are employed for this purpose:

(a) In formula I wherein X represents an atom of oxygen or sulfur, Y is an atom of oxygen, A represents either a 3 membered straight chain or a part of a ring, the amino group B is a tertiary amine and R, $R^1$ and $R^2$ are as designated above, the compound of interest may be obtained by an intramolecular substitution reaction of fluorinated aminoalcohols of the general formula VI

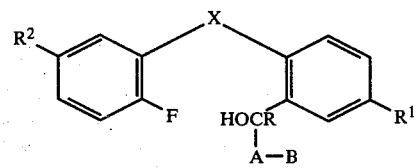

wherein

R, $R^1$ and $R^2$ are as designated above,

X is either oxygen or sulfur and the A—B unit is as described in formula I with the above noted limitation (A is a 3 membered hydrocarbon residue and B is a tertiary amino group which does not contain Grignard reactive functional groups as N substituents). This reaction is effected by reaction with sodium hydride in an inert solvent, for example, dimethylformamide, at a temperature ranging from 50°–100° C. in an inert ambient. A preferred temperature is 70° C. in combination with a nitrogen ambient.

The aminoalcohols of formula VI may be prepared by reaction of carbonyl compounds (aldehydes or ketones) of the general formula VII,

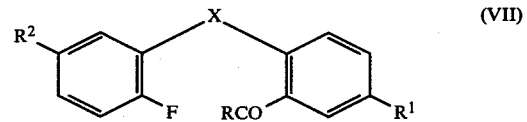

wherein R, $R^1$, $R^2$ and X are as designated in formula VI, with a Grignard reagent of the general formula VIII, ZMg—A—B (VIII)

wherein Z is an atom of chlorine or bromine and A—B is as designated in formula VI. These Grignard reactions are typically carried out in absolute boiling tetrahydrofuran. It should be noted that the carbonyl compounds of formula VII are in most cases novel compounds and methods for their preparation are set forth in the Examples.

(b) Compounds of formula I, wherein X is an atom of oxygen or sulfur, Y is an atom of sulfur or an $SO_2$ group, R is hydrogen, $R^1$ and $R^2$ are as designated in formula I and A—B is as designated in formula I with the limitation that the connecting member —A— must be at least a two-membered hydrocarbon fragment with B being a tertiary amino group containing as the N-substituent, or as N-substituents, only unreactive hydrocarbon residues, are prepared by alkylation of compounds of the general formula IX,

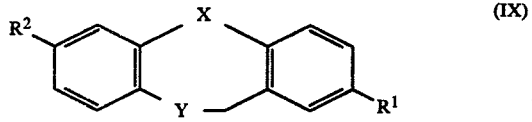

wherein X is an atom of oxygen or sulfur, Y is an atom of sulfur or an SO$_2$ A group, and R$^1$ and R$^2$ are as designated in formula I, with aminoalkyl halogenides of the general formula X,

wherein Z represents an atom of chlorine or bromine and A—B is as designated in formula I with the limitation that the connecting member —A— must be at least a two-membered hydrocarbon fragment and B is a tertiary amino group containing as the N-substituent or as N-substituents only unreactive hydrocarbon residues. In the alkylation of compounds of formula IX, wherein Y=S, it is necessary to use butyllithium for generating the necessary carbanion and the reaction must be carried out in ether. In the alkylation of compounds of formula IX, wherein Y=SO$_2$, milder bases may be used (such as sodium hydride) for the formation of the carbanion and the reaction effected in dimethylformamide. The starting compounds of formula IX are in most cases novel and are obtained by procedures described in the Examples. Sulfones of the formular IX (Y=SO$_2$) are prepared by oxidation of the corresponding sulfides (wherein X=—O—), typically with hydrogen peroxide in boiling acetic acid. The starting aminoalkyl halogenides of formula X are known.

(c) Compounds of the formula I, wherein X is an atom of oxygen or sulfur, Y is an atom of sulfur, R is hydrogen, R$^1$ and R$^2$ are as designated in formula I and the residue —A—B has the same meaning as in formula VI, may be prepared by chlorination of compounds of general formula XI,

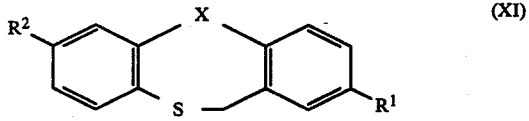

wherein X is an atom of oxygen or sulfur and R$^1$ and R$^2$ are as designated in formula I, so yielding the chloro derivatives of formula XII,

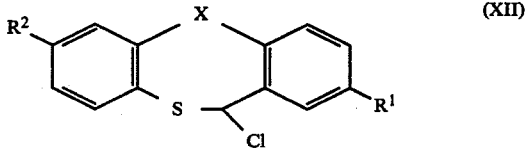

wherein the symbols have the same meaning as in the formula XI. The resultant crude chloro derivatives, which are not isolated in pure state, are subjected to treatment with Grignard reagents of the general formula VIII. The chlorination is preferably carried out with reagents like sulfuryl chloride or N-chlorosuccinimide in unreactive solvents, advantageously in tetrachloromethane, benzene and similar reagents. The reactions with Grignard reagents proceed most favorably in tetrahydrofuran. The starting compounds of formula XI are included in compounds of the previously mentioned formula IX and they are accessible in the same manner as compounds of formula IX.

(d) Compounds of formula I, wherein B is a secondary amino group (i.e. B=NHCH$_3$ or R$^3$=H), may be prepared from the corresponding N-methyl derivatives which are accessible by some of the previously mentioned methods, by a two-step procedure, wherein the first stage involves treatment with ethyl chloroformate in boiling benzene and the second stage involves the alkaline hydrolysis of the resultant N-desmethyl N-(ethoxycarbonyl) derivatives of formula I, wherein B=N(CH$_3$)COOC$_2$H$_5$, or wherein R$^3$=COOC$_2$H$_5$. These carbamates have not been isolated in the pure state but only as neutral products of the first stage of the reaction sequence. Potassium hydroxide in the form of a very concentrated solution in ethanol is used advantageously for the purpose of the alkaline hydrolysis; the hydrolysis is carried out at the boiling point of the solution.

(e) Compounds of formula I, wherein R$^3$ is hydroxyalkyl, are typically prepared by alkylation of the corresponding secondary amines (I, R$^3$=H) with halogenoalkanols, e.g. with 2-bromoethanol. The reaction is advantageously carried out in boiling acetone in the presence of alkaline reagents capable of binding the hydrogen halogenide. Potassium carbonate is preferred for this purpose.

(f) Compounds of formula I, wherein R$^3$ is hydroxyalkyl, may also be prepared by alkylation of the corresponding secondary amines (I, R$^3$=H) with the corresponding halogenoaldehydes or halogenoketones with subsequent reduction of the carbonyl intermediates obtained. For alkylation, conditions similar to those in (e) with the reduction being carried out by conventional methods for the preparation of alcohols from aldehydes or ketones, advantageteously with sodium borohydride.

(g) Compounds of general formula I, wherein R$^3$=acyloxyalkyl, may be prepared by acylation of compounds according to methods (e) and (f), above, i.e. of compounds of the formula I, wherein R$^3$ is hydroxyalkyl, with the corresponding fatty acids or their reactive derivatives (halogenides, anydrides, re-esterification with esters). An acylation with free acids under conditions of "azeotropic" esterification which involves distillation of a mixture of the starting aminoalcohol, the fatty acide and xylene, wherein the distilling xylene removes the water, formed by the reaction, in the form of an azeotropic mixture is a preferred procedure.

(h) Compounds of the formula I, wherein R$^3$ is methyl and R$^4$ is a hydroxyl group, may be prepared by reaction of compounds of general formula XI with butyllithium in ether and by subsequent treatment with 1-methyl-4-piperidone.

(I) Compounds of formula I, wherein X is an atom of oxygen or sulfur, Y is an atom of sulfur, R=H, R$^1$ and R$^2$ are as designated in formula I, A is a methylene group (—CH$_2$—) and B is a dimethylamino group, may be prepared by reduction of dimethylamides of the general formula XII-A,

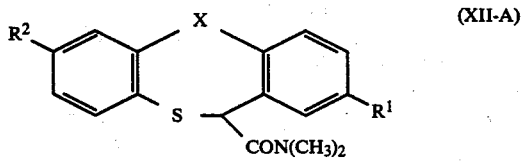

wherein X is an atom of oxygen or sulfur and $R^1$ and $R^2$ are as designated in formula I. Complex hydrides may be used as reducing agents, such as lithium aluminium hydride or diborane, generated from sodium borohydride and boron trifluoride etherate. The starting amides of formula XII-A are obtained from acids of formula XIII,

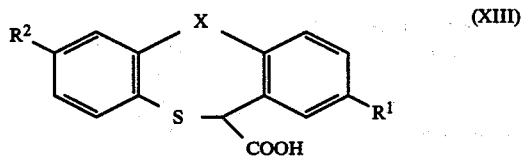

wherein X, $R^1$ and $R^2$ are as designated in formula XII-A, by a two-step procedure, wherein the first stage involves reacting the acids with thionyl chloride to yield crude acid chlorides. The resultant chloride is then reacted with dimethylamine in an inert solvent, typically benzene, to yield the desired dimethylamides. The acids of formula XIII are in some cases novel and in other cases known, references being given in the corresponding examples.

(j) Compounds of formula I, wherein X is a sulfoxide group, SO, or a sulfone group, $SO_2$, and Y is simultaneously an atom of oxygen, may be prepared by oxidation of the corresponding compounds of formula I, wherein X is an atom of sulfur. For oxidation to a sulfoxide, a mild excess of hydrogen peroxide in acetic acid or in an aqueous solution of methanesulfonic acid at room temperature is used. Other oxidation reagents suitable for this reaction may also be used, for example, m-chloroperbenzoic acid, periodic acid. For the oxidation to a sulfone, it is necessary to use an excess of hydrogen peroxide and the reaction must be carried out in boiling acetic acid.

(k) The N-oxides, derived from compounds of formula I, which likewise are included in this invention, are prepared by oxidation of solutions of bases of formula I in ethanol with a mild excess of hydrogen peroxide at room temperature.

The method of preparation of the salts, which are also included in this invention, involves neutralization of bases of formula I by the corresponding inorganic or organic acids in suitable solutions, typically in ethanol or in a mixture of ethanol and ether. The salts obtained are crystalline and suitable for the characterization of bases of formula I. The identity of all new compounds, described in the invention, i.e. of the final products and also of the new intermediates, was confirmed by analyses, and by commonly used spectral methods (UV, IR, $^1$H-NMR and MS spectra).

The invention will be more readily understood by reference to the following exemplary embodiments. It will be appreciated by those skilled in the art that these embodiments are set forth solely for purposes of exposition and are not to be construed as limiting.

EXAMPLE 1

11-(3-Dimethylaminopropyl)-11H-dibenzo(b,e)-1,4-dioxepin

A stirred mixture of 3.4 g of sodium hydride and 100 ml of dimethylformamide was treated for 6 hours at 70° C. in an inert nitrogen atmosphere with 15.1 g 1-/2-(2-fluorophenoxy)phenyl/-4-dimethylaminobutanol and after standing overnight was poured into 2.5 l of ice-cold water. The product was extracted with ether, the extracted dried with potassium carbonate and evaporated. The remaining oil (14.3 g) was chromatographed on a column of 500 g neutral aliminium oxide (activity II). By elution with benzene, 3.28 g of a homogeneous oily product was obtained which was neutralized with maleic acid in a mixture of ehtanol and ether to yield 3.22 g of pure hydrogen maleate which crystallized from a mixture of acetone and ether and melted at 82°–84° C.

The 1-/2-(2-fluorophenoxy)phenyl/-4dimethylaminobutanol is a novel substance and may be prepared by the following procedure:

A solution of 44.2 g 2-(2-fluorophenoxy)benzoid acid (F. L. Allen et al., Tetrahedron 6,315, 1959) in 65 ml tetrahydrofuran is slowly treated at 10°–25° C. while stirring with 7.22 g of sodium borohydride and after 30 minutes of stirring a solution of 36 g boron trifluoride etherate in 17 ml tetrahydrofuran is added dropwise. The mixture is stirred for 3 hours at 15°–20° C., and after standing overnight, is decomposed at 8° C. with 20 ml 5% hydrochloric acid added dropwise, is diluted with 200 ml of water and extracted with benzene. The extract is washed with a 5% sodium hydroxide solution, dried with magnesium sulfate and evaporated. Distillation of the residue affords 31.7 g (76%) 2-(2-fluorophenoxy)benzyl alcohol boiling at 127°–129° C./30 Pa.

A solution of 31.5 g of the resultant alcohol in 30 ml of acetic acid is treated dropwise for 30 minutes while stirring with a solution of 160 g of ceric ammonium nitrate in 600 ml of 50% acetic acid, the mixture being stirred for 1 hour at room temperature. Then, the mixture was heated for 2 hours in a boiling water bath. After cooling, it was extracted with benzene, the extract being washed with a 5% solution of sodium carbonate, and dried with potassium carbonate and evaporated. Distillation of the residue yielded 27.6 g of pure 2-(2-fluorophenoxy)benzaldehyde boiling at 120°–123° C./105 Pa.

A Grignard reagent was prepared by boiling a mixture of 1.7 g of magnesium, 8.5 g of 3-dimethylaminopropyl chloride and 30 ml of tetrahydrofuran (initiated with a drop of 1,2-dibromoethane and a crystal of iodine) for 2 hours. Next, the reagent was treated with a solution of 10.8 g of the preceding aldehyde in 20 ml of tetrahydrofuran and the mixture refluxed for 4 hours. After cooling, it was decomposed with a 20% ammonium chloride solution and the product isolated by extraction with ether. Evaporation of the extract resulted in 15.1 g 1-/2-(2-fluorophenoxy)phenyl/-4-dimethylaminobutanol which is used for further work in its crude stage. For characterization, a sample was neutralized with 2,4,6-trinitrobenzoic acid to obtain the crystalline 2,4,6-trinitrobenzoate which crystallized from a mixture of ethanol and ether and melts at 96°–98° C. with decomposition.

EXAMPLE 2

6-(3-Dimethylaminopropyl)-6H-dibenzo(b,e)-1,4-oxathiepin

A solution of 15.75 g of crude 1-/2-(fluorophenylthio)phenyl/-4-dimethylaminobutanol in 80 ml dimethylformamide was added dropwise over a period of 6 hours to a stirred suspension of 2.0 g of sodium hydride in 120 ml dimethylformamide at 70° C. in a nitrogen atmosphere. Heating to 70° C. was continued for 8 hours, the mixture poured into 2.5 l of water, the separated semi-solid substance dissolved in ether, the solution dried with potassium carbonate and evaporated. The remaining oil (15.1 g) was chromatographed on a column of 500 g of neutral aluminium oxide (activity II). The desired compound (7.94 g) was eluted with benzene and neutralized with maleic acid in acetone to yield 9.5 g hydrogen maleate crystallizing from a mixture of acetone and ether and melting at 117°–118° C.

The starting 1-/2-(2-fluorophenylthio)phenyl/-4-dimethylaminobutanol is a novel substance which may be prepared in the following manner:

A solution of 43.8 g 2-fluorothiophenol (I. Cervena et al., Collect. Czech. Chem. Commun. 44, 2139, 1979) in 85 ml of hexamethylphosphoramide is treated in a nitrogen atmosphere first with a solution of 13.6 g sodium hydroxide in 26 ml of water and then with 45.0 g of 2-chlorobenzaldehyde. Then the mixture is heated for 3.5 hours to 100° C. It is next poured into 500 ml of water and the product extracted with benzene. The extract is dried with magnesium sulfate and evaporated. The residue crystallizes after mixing with 120 ml of petroleum ether. There are obtained 57.1 g (77%) 2-(2-fluorophenylthio)benzaldehyde, crystallizing from benzene and melting in pure state at 56°–57° C.

A Grignard reagent is prepared by boiling a mixture of 1.7 g of magnesium, 8.5 g 3-dimethylaminopropyl chloride and 30 ml of tetrahydrofuran for 3 hours. The stirred reagent is treated dropwise with a solution of 11.6 g of the aldehyde from the previous step in 20 ml of tetrahydrofuran for 30 minutes. Then, the mixture is refluxed for 3 hours and decomposed after standing overnight with a 20% solution of ammonium chloride. The product is isolated by extraction with ether, the extract dried with potassium carbonate and evaporated. The crude 1-/2-(2-fluorophenylthio)phenyl/-4-dimethylaminobutanol is obtained in theoretical yield (16.0 g) and is used for further work in this state. Neutralization of a sample with 2,4,6-trinitrobenzoic acid affords the crystalline 2,4,6-trinitrobenzonate which crystallizes from a mixture of ethanol and ether and melts at 103°–103.5° C. with decomposition.

EXAMPLE 3

6-(3-Piperidinopropyl)-6H-dibenzo(b,e)-1,4-oxathiepin

A solution of 14.0 g 1-/2-(2-fluorophenylthio)phenyl/-4-piperidinobutanol in 80 ml dimethylformamide was added dropwise at 70° C. over a time period of 4.5 hours to a stirred suspension of 3.0 g of sodium hydride in 100 ml dimethylformamide in a nitrogen atmosphere. The mixture was stirred for 7 hours at 70° C., decomposed by pouring into water and the product extracted with ether. The extract was then dried with potassium carbonate and evaporated. A homogeneous oily product was obtained in a yield of 12.25 g (93%). The hydrogen maleate was obtained by neutralization with maleic acid, was recrystallized from a mixture of ethanol and ether and melted at 145°–147° C.

The starting 1-/2-(2-fluorophenylthio)phenyl/-4-piperidinobutanol is a novel substance and is prepared in the following manner:

A solution of a Grignard reagent is prepared by boiling a mixture of 1.46 g of magnesium, 9.7 g of 3-piperidinopropyl chloride (P. Offner and E. Walten, J.Chem. Soc. 1950, 2158) and 25 ml of tetrahydrofuran (initiated with a crystal of iodine); the mixture is refluxed for 3 hours. A solution of 9.3 g 2-(2-fluorophenylthio) benzaldehyde (of Example 1) in 15 ml tetrahydrofuran is then added dropwise and the mixture refluxed for 3 hours. After standing overnight, it is diluted with 15 ml of ether, decomposed slowly by the addition of 50 ml of 20% ammonium chloride solution and extracted with ether. The extract is dried with potassium carbonate and evaporated. The crude 1-/2-(2-fluorophenylthio)phenyl/-4-piperidinobutanol is obtained in a theoretical yield (14.3 g); it crystallizes slowly by standing. The pure substance is obtained by recrystallization from cyclohexane and it melts at 93°–94° C.

EXAMPLE 4

6-(1-Methyl-3-piperidylmethyl)-6H-dibenz(b,e)-1,4-oxathiepin

A solution of 13.8 g of 1-/2-(2-fluorophenylthio) phenyl/-2-(1-methyl-3-piperidyl)ethanol in 80 ml dimethylformamide was added dropwise over a 7 hour time period to a stirred suspension of 3.0 g of sodium hydride in 100 ml of dimethylformamide at 70° C. in a nitrogen atmosphere. The mixture was stirred for 8 hours at 70° C. and decomposed by pouring into water. The product was extracted with ether, the extract dried with potassium carbonate and evaporated. The remaining oil was chromatographed on a column of 500 g of neutral aluminium oxide (activity II). Benzene and then chloroform eluted 10.84 g stereoisomeric bases from which the prevailing component (base A) crystallized from a mixture of Cyclohexane and petroleum ether, the melting point being 102°–103.5° C. The majority of the mixture of bases was transformed by neutralization with oxalic acid to the hydrogen oxalate which crystallized from ethanol and melted in the pure state at 192°–193° C. It was the oxalate of the prevailing base A. From the mother liquors, a different hydrogen oxalate was obtained which crystallized in needles and was purified by crystallization from a mixture of acetone and ethanol and then from ethanol only: hydrogen oxalate of the minor base B melted in the pure state at 174°–175° C.

The starting 1-/2-(2-fluorophenylthio)phenyl/-2-(1-methyl-3-piperidyl)ethanol is a novel compound and may be obtained by the following procedure:

A solution of a Grignard reagent is prepared by reaction of 1.46 g of magnesium and 8.86 g of 1-methyl-3-(chloromethyl)piperidine (L. Noval et al, Cesk.Farm. 6, 365, 1957) in 25 ml of tetrahydrofuran (initiated with a grain of iodine) by refluxing for 3 hours. A solution of 9.30 g of 2-(2-fluorophenylthio)benzaldehyde (of Example 2) in 15 ml of tetrahydrofuran is added dropwise and the mixture refluxed for 3 hours. After cooling it is diluted with 50 ml of ether, decomposed with 50 ml of 20% ammonium chloride solution and extracted with ether. The extract is dried with potassium carbonate and evaporated. The oily product is obtained in a theoretical yield (13.8 g) and is used for further work without characterization.

EXAMPLE 5

6-(1-Methyl-4-piperidyl)-6H-dibenz(b,e)-1,4-oxathiepin

A stirred suspension of 2.5 g of sodium hydride in 100 ml of dimethylformamide was treated for 9 hours at 70° C. in a nitrogen atomsphere with a solution of 13.25 g α-(1-methyl-4-piperidyl)-2-(2-fluorophenylthio) benzyl alcohol in 80 ml dimethylformamide, added dropwise, and the mixture stirred at the same temperature for an additional 5 hours. It was then decomposed by pouring into 2.5 ml of water, extracted with ether, the extract dried with potassium carbonate and evaporated. The residue (12.1 g) was chromatographed on a column of 500 g of neutral aluminium oxide (activity II). Elution with benzene and with a mixture of benzene and chloroform yielded 7.33 g of the desired base which was crystallized from a mixture of cyclohexane and petroleum ether and melted in a pure state at 77°–79° C. The crystalline hydrogen maleate was obtained by neutralization with maleic acid; it melted in a pure state at 152°–153° C.(acetone-ether).

The starting α-(1-methyl-4-piperidyl)-2-(2-fluorophenylthio)-benzyl alcohol is a novel compound and is prepared in the following manner:

A solution of a Grignard reagent is prepared by reaction of 1.46 g of magnesium with 8.0 g of 4-chloro-1-methylpiperidine (M. McElvain and K. Rorig, J.Amer.-Chem. Soc. 70, 1826, 1948) in 25 ml of tetrahydrofuran. It is treated while stirring for 30 minutes with a solution of 9.3 g of 2-(2-fluorophenylthio)benzaldehyde (of Example 2) in 15 ml tetrahydrofuran, added dropwise, and the mixture refluxed for 3 hours. After standing overnight, it is decomposed by addition of 50 ml of 20% ammonium chloride solution and the product extracted with ether. The extract is dried with potassium carbonate and evaporated. The residue (13.25 g -100%-) is the crude oily α-(1-methyl-4-piperidyl)-2-(2-fluorophenylthio)benzyl alcohol which is crystallized from cyclohexane and melts in a pure state at 111°–114° C.

EXAMPLE 6

8-Chloro-6-(1-methyl-4-piperidyl)-6H-dibenz(b,e)-1,4-oxathiepin

A solution of 26.8 g α-(1-methyl-4-piperidyl)-2-(2-fluorophenylthio)-5-chlorobenzyl alcohol in 130 ml dimethylformamide was slowly added to a stirred suspension of 5.7 g sodium hydride in 180 ml dimethylformamide in a nitrogen atmosphere. The mixture was stirred for 14 hours at 70° C., decomposed by pouring into water and extracted with ether. The extract was washed with water, dried with potassium carbonate and evaporated. The residue (20 g oil) was chromatographed on a column of 1 kg of neutral aluminium oxide (activity II). The least polar product was first removed by elution with benzene and the homogeneous desired base (6.57 g) then eluted. Thereafter, there were obtained 3.52 g of a mixture of this base with a more polar component. This mixture was then rechromatographed on a column of 220 g of silica gel. Elution with chloroform yielded 2.18 g of the desired product, the total yield of which was thus increased to 8.75 g. Neutralization of this oily base with maleic acid yielded the crystalline hydrogen maleate, m.p. 188.5°–190° C. (acetone-ether-ethanol).

The starting α-(1-methyl-4-piperidyl)-2-(2-fluorophenylthio)-5-chlorobenzyl alcohol is a novel compound and is obtained in the following manner:

solution of 3.4 g sodium hydroxide in 6 ml of water and then 14 g of 2,5-dichlorobenzaldehyde (H. Erdmann, Justus Liebigs Ann. Chem. 272, 155, 1893) are added to a solution of 10.8 g 2-fluorothiophenol (reference above) in 20 ml of hexamethylphosphortriamide. Then, the mixture is heated for 5.5 hours to 100° C. After cooling it is diluted with 150 ml of water and extracted with benzene. The extract is washed with a 5% sodium hydroxide solution and with water, dried with magnesium sulfate and evaporated. Crude 2-(2-fluorophenylthio) 5-chlorobenzaldehyde is obtained which is then recrystallized from 20 ml ethanol; 16.0 g, m.p. 85.5°–88° C. A further crystallization affords an analytically pure product, m.p. 87°–88° C.

A solution of the Grignard reagent is obtained by reaction of 2.7 g of magnesium with 13.7 g of 4-chloro-1-methylpiperidine (reference above) in 80 ml of tetrahydrofuran and is treated for 10 minutes with a solution of 20 g of 2-(2-fluorophenylthio)-5-chlorobenzaldehyde in 40 ml of tetrahydrofuran, added dropwise. The mixture is refluxed for 4.5 hours and after standing overnight it is decomposed by the addition of 20% of ammonium chloride solution and extracted with benzene. The extract is washed with water, dried with potassium carbonate and evaporated. There are obtained 27.4 g (100%) of crude oily α-(1-methyl-4-piperidyl)-2-(2-fluorophenylthio)-5-chlorobenzyl alcohol which may be characterized by conversion to the crystalline 2,4,6-trinitrobenzoate, m.p. 100°–101.5° C. by decomposition (ethanol-ether).

EXAMPLE 7

8-Chloro-6-methyl-6-(3-dimethylaminopropyl)-6H-dibenz(b,e)-1,4-oxathiepin

A solution of 13.4 g of 2-/2-(2-fluorophenylthio)-5-chlorophenyl/-5-dimethylaminopentan-2-ol in 80 ml of dimethyl=formamide was added dropwise for 7 hours at 70° C. to a stirred suspension of 3.0 g of sodium hydride in 100 ml of dimethylformamide and the mixture stirred for an additional 7 hours at the same temperature. After cooling it was decomposed by pouring into water, the product extracted with ether, the extract dried with potassium carbonate and the ether evaporated. The residue was then chromatographed on a column of 450 g of neutral aluminium oxide (activity II). Elution with benzene first removed the less polar impurities and yielded 2.03 g of a homogeneous oily base which was neutralized with oxalic acid yielding crystalline hydrogen oxalate, m.p. 78°–80° C. (acetone-ether).

The starting 2-/2-(2-fluorophenylthio)-5-chlorphenyl/-5-dimethylaminopentan-2-ol is a novel compound which is prepared in the following manner:

A solution of a Grignard reagent is prepared by reaction of 1.46 g of magnesium with 7.3 g of 3-dimethylaminopropyl chloride in 25 ml of tetrahydrofuran and is treated with a solution of 11.2 g 2-(2-fluorophenylthio)-5-chloroacetophenone (I. Cervena et al., Collect.Czech.Chem.Commun.44, 2139,1979) in 20 ml tetrahydrofuran. The mixture is refluxed for 4 hours and, after cooling, it is decomposed by the addition of 50 ml of 20% ammonium chloride solution and extracted with ether. The extract is dried with potassium carbonate and evaporated. There are obtained 13.2 g (90%) of oily 2-/2-(2-fluorophenylthio)-5-chlorophenyl/-5-dimethylaminopentan-2-ol. For its characterization, the hydrogen oxalate is suitable and is obtained by neutralization of the base with oxalic acid; m.p. 127°–131° C. (acetone-ether).

EXAMPLE 8

8-Chloro-6-methyl-6-(1-methyl-4-piperidyl)-6H-dibenz(b,e)-1,4-oxathiepin

A solution of 20 g of crude 1-/2-(2-fluorophenylthio)-5-chlorophenyl/-1-(1-methyl-4-piperidyl)ethanol in 120 ml of dimethylformamide was added dropwise for 6 hours at 70° C. in a nitrogen atmosphere to a stirred suspension of 4.5 g sodium hydride in 150 ml of dimethylformamide. The mixture was stirred for 8 hours at the same temperature. After cooling, it was decomposed by pouring on to water and the product extracted with benzene. The extract was dried with potassium carbonate and evaporated. The residue was chromatographed on a column of 500 g of neutral aluminium oxide (activity II). Elution with benzene first removed 2.25 g of the less polar fractions and yielded 4.45 g of the crude product which was rechromatographed on silica gel (90 g) and yielded a homogeneous product. Neutralization with oxalic acid yielded crystalline hydrogen oxalate, m.p. 167°–169° C. (acetone-ether).

The starting 1-/2-(2-fluorophenylthio)-5-chlorophenyl/-1-(1-methyl-4-piperidyl)ethanol is a novel compound which is prepared in the following manner:

A solution of a Grignard reagent is prepared in the usual manner by reaction of 2.92 g of magnesium with 16.03 g of 4-chloro-1-methylpiperidine (reference above) in 50 ml of tetrahydrofuran (initiated by a grain of iodine). It was treated with a solution of 22.5 g of 2-(2-fluorophenylthio)-5-chloroacetophenone (reference above) in 40 ml of tetrahydrofuran and the mixture refluxed for 3 hours. After standing overnight, it was decomposed by the addition of 100 ml of 20% ammonium chloride solution and then extracted with ether. The extract was dried with potassium carbonate and evaporated. 24.8 g (82%) of crude oily 1-/2-(2-fluorophenylthio)-5-chlorophenyl/-1-(1-methyl-4-piperidyl)ethanol was obtained which was used for further work without purification.

EXAMPLE 9

8-Methoxy-6-(1-methyl-4-piperidyl)-6H-dibenz(b,e)-1,4-oxathiepin

A solution of 23.7 g α-(1-methyl-4-piperidyl)-2-(2-fluorophenylthio)-5-methoxybenzyl alcohol in 120 ml dimethylformamide was added dropwise for 4 hours at 70° C. in a nitrogen atmosphere to a stirred suspension of 5.4 g of sodium hydride in 170 ml of dimethylformamide and the mixture is stirred for 11 hours at the temperature mentioned. It was then decomposed by pouring into water and extracted with ether. The extract was dried with potassium carbonate and evaporated. The residue was processed by a combination of crystallization from a mixture of cyclohexane and petroleum ether and chromatography of the mother liquors on a column of 500 g of neutral aluminium oxide (activity II); the desired compound was eluted with a mixture of benzene and chloroform. There were obtained in total 17.1 g of the desired base which crystallized from a mixture of cyclohexane and petroleum ether and which melted in a pure state at 103°–105° C. By neutralization with maleic acid it yielded the crystalline hydrogen maleate, m.p. 182.5°–183.5° C. (acetone-ethanol).

The starting α-(1-methyl-4-piperidyl)-2-(2-fluorophenylthio)-5-methoxybenzyl alcohol is a novel compound which may be prepared in the following manner:

A mixture of 27.1 g 2-bromo-5-methoxybenzaldehyde (T. Kametani et al, Chem. Pharm. Bull. 23, 2634, 1975), 17.0 g 2-fluorothiophenol (reference above), 19.3 g of anhydrous potassium carbonate, 100 ml of dimethylformamide and 3 g of copper is stirred and heated for 6 hours in a bath having a temperature of 150° C. After partial cooling, the mixture is diluted with water and benzene, filtered, the organic layer of the filtrate separated and the aqueous one extracted with benzene. The combined benzene solutions are washed with water, dried with magnesium sulfate and evaporated. The oily product obtained is chromatographed on a column of 500 g of neutral aluminium oxide (activity II). With benzene, there are eluted 18.9 g (57%) of homogeneous 2-(2-fluorophenylthio)-5-methoxybenzaldehyde, boiling at 153° C./40 Pa and crystallizing from a mixture of cyclohexane and petroleum ether, m.p. 58°–59° C.

A solution of the Grignard reagent is prepared by reaction of 2.5 g of magnesium with 13.35 g of 1-methyl-4-chloropiperidine (reference above) in 80 ml of tetrahydrofuran in the usual manner. Over 15 minutes with stirring, a solution of 18.2 g of 2-(2-fluorophenylthio)-5-methoxybenzaldehyde in 40 ml tetrahydrofuran is added dropwise and the mixture refluxed for 4 hours. After cooling, it is decomposed with 20% ammonium chloride solution and extracted with benzene. The extract is dried with potassium carbonate and evaporated. There are obtained 23.7 g (100%) crude oily α-(1-methyl-4-piperidyl)-2-(2-fluorophenylthio)-5-methoxybenzyl alcohol which is used for further work without purification.

EXAMPLE 10

8-Trifluoromethyl-6-(1-methyl-4-piperidyl)-6H-dibenz(b,e)-1,4-oxathiepin

A solution of 23.2 g of crude α-(1-methyl-4-piperidyl)-2-(2-fluorophenylthio)-5-trifluoromethylbenzyl alcohol in 100 ml of dimethylformamide was added dropwise over 6 hours at 70° C. in an atmosphere of nitrogen to a stirred suspension of 4.5 g of sodium hydride in 140 ml of dimethylformamide and the mixture stirred for another 16 hours at the temperature given. It was decomposed by pouring into water and extracted with a mixture of benzene and ether. The extract was washed with water, dried with potassium carbonate and evaporated. The residue was then chromatographed on a column of 500 g of neutral aluminium oxide (activity II). Elution with benzene removed the less polar components and elution with a mixture of benzene and chloroform then yielded 1.48 g of the homogeneous desired compound. A crystalline hydrogen oxalate was obtained by neutralization with oxalic acid, m.p. 215.5°–216.5° C. with decomposition (acetone-ethanol).

The starting α-(1-methyl-4-piperidyl)-2-(2-fluorophenylthio)-5-trifluoromethylbenzyl alcohol is a novel compound which may be obtained in the following manner:

3-Amino-4-chlorobenzotrifluoride (A.E. Porai-Kosic et al., Zh. Prikl. Khim. 28, 969, 1955; Chem. Abstr. 50, 4880, 1956) (222 g) is slowly added to a stirred solution of 260 ml hydrochloric acid in 2330 ml water. The resultant suspension of the hydrochloride is cooled, treated with 450 g of ice and diazotized at 0°–5° C. with a solution of 80 g of sodium nitrite in 110 ml of water, added dropwise. The mixture is stirred for 1 hour at 0°–5° C. and treated with a cooled solution of 100 g of sodium acetate trihydrate in 150 ml water. The undissolved substance is separated (distillation recovers 70.8 g starting 3-amino-4-chlorobenzotrifluoride) and the solution of the diazonium salt is added while stirring at 10°–20° C. to a solution of formaldoxime (prepared by boiling a mixture of 57.5 g paraformaldehyde, 131.5 g of hydroxylamine hydrochloride, 255 g of sodium acetate trihydrate and 850 ml of water for 15 minutes) and a solution of 32.5 g cupric sulfate pentahydrate, 5 g sodium of sulfite and 800 g of sodium acetate in 300 ml water with the addition of 300 ml of toluene. The mixture is stirred for 2 hours, 1100 ml of hydrochloric acid added and the mixture refluxed for 2 hours. It is then distilled with steam and the distillate extracted with benzene. The extract is washed with a 5% sodium hydrogen carbonate solution and evaporated. The residue is dissolved in 200 ml ether and the solution stirred for 2 hours with 450 ml of 40% sodium hydrogen sulfite solution. After standing overnight, the precipitated addition product is filtered with suction, washed with ether, and suspended in 1 liter of water, then, 200 ml of hydrochloric acid are added and the mixture refluxed for 2 hours. After cooling, it is extracted with benzene, the extract dried with magnesium sulfate, evaporated and the residue processed by distillation. There are obtained 49.1 g (31% per conversion) of 2-chloro-5-trifluoromethylbenzaldehyde, b.p. 93°–96° C./2.1 kPa.

A solution of 12.2 g of 2-fluorothiophenol (of Example 2, reference above) in 25 ml of hexamethylphosphortriamide is treated with a solution of 4.0 g sodium hydroxide in 7 ml of water and then with 16.8 g of 2-chloro-5-trifluoromethylbenzaldehyde. The mixture is stirred for 6 hours at 100° C., poured into water and the product extracted with benzene. Evaporation of the extract yields 25.5 g (97%) of crude 2-(2-fluorophenylthio)-5-trifluoromethylbenzaldehyde melting at 130°–132° C. By crystallization from a mixture of benzene and petroleum ether, the analytically pure compound is obtained melting at the same temperature.

A solution of the Grignard reagent is prepared by a reaction of 12.0 g 4-chloro-1-methylpiperidine with 2.3 g of magnesium in 70 ml of tetrahydrofuran and is treated for 10 minutes with a solution of 17.4 g 2-(2-fluorophenylthio)-5-trifluoromethylbenzaldehyde in 40 ml of tetrahydrofuran added dropwise. The mixture is refluxed for 4 hours and after cooling, decomposed with a 20% ammonium chloride solution and extracted with benzene. The extract is dried with potassium carbonate and evaporated. There are obtained 23.2 g (100%) crude oily α-(1-methyl-4-piperidyl)-2-(2-fluorophenylthio)-5-trifluoromethylbenzyl alcohol which is used in this state for the final reaction.

EXAMPLE 11

2-Fluoro-8-chloro-6-(1-methyl-4-piperidyl)-6H-dibenz(b,e)-4-oxathiepin

A solution of 21.2 g of crude α-(1-methyl-4-piperidyl)-2-(2,5-diflurophenylthio)-5-chlorobenzyl alcohol in 100 ml of dimethylformamide was added while stirring at 70° C. in an atmosphere of nitrogen to a suspension of 3.9 g of sodium hydride in 140 ml of dimethylformamide. The resultant mixture was stirred under the conditions described for 14 hours. It was then decomposed by pouring into water and extracted with ether. The extract was washed with water, dried with potassium carbonate and evaporated. The oil obtained was chromatographed on a column of 500 g of neutral aluminium oxide (activity II). Elution with benzene first removed 2.13 g of a less polar component and then yielded 7.1 g of the desired base which crystallized from cyclohexane and melted in a pure state at 127°–129° C. Neutralization with maleic acid yielded the hydrogen maleate which crystallized from a mixture of acetone and ether or from ethanol and melted in a pure state at 190°–192° C.

The starting α-(1-methyl-4-piperidyl)-2-(2,5-difluorophenylthio)-5-chlorobenzyl alcohol is a novel compound and is prepared by the following procedure:

The solution of 13.1 g of 2,5-difluorothiophenol (I. Cervena et al., Collect. Czech. Chem. Commun. 45, 2688, 1980) in 20 ml hexamethylphosphortriamide is treated with a solution of 3.6 g of sodium hydroxide in 6 ml of water and then with 13.65 g of 2,5-dichlorobenzaldehyde (of Example 6, reference above). Then, the mixture is heated while stirring for 5.5 hours to 100° C. It is then diluted with 150 ml of water and extracted with benzene. The extract is washed with a 5% sodium hydroxide solution and water, dried with magnesium sulfate and evaporated. The residue is crystallized from a mixture of benzene and petroleum ether. There are obtained 16.4 g (74%) 2-(2,5-difluorophenylthio)-5-chlorobenzaldehyde which melts in a pure state at 88°–90° C.

A solution of a Grignard reagent is prepared by reaction of 11.35 g of 4-chloro-1-methylpiperidine with 2.3 g of magnesium in 70 ml of tetrahydrofuran and is then treated for 10 minutes with a solution of 16.1 g 2-(2,5-difluorophenylthio)-5-chlorobenzaldehyde in 40 ml of tetrahydrofuran, added dropwise. The mixture is refluxed for 4 hours and, after cooling, decomposed with a 20% ammonium chloride solution and extracted with benzene. The extract is washed with water, dried with potassium carbonate and evaporated. There are obtained 21.7 g (100%) crude oily α-(-methyl-4-piperidyl)-2-(2,5-difluorophenylthio)-5-chlorobenzyl alcohol which is used in this state for the final step.

EXAMPLE 12

2-Fluoro-8-methoxy-6-(1-methyl-4-piperidyl)-6H-dibenz(b,e)-1,4-oxathiepin

A solution of 12.5 g of α-(1-methyl-4-piperidyl)-2-(2,5-difluorophenylthio)-5-methoxybenzyl alcohol in 60 ml of dimethylformamide was added at once to a suspension of 2.5 g of sodium hydride in 80 ml of dimethylformamide while stirring in a nitrogen atmosphere. The mixture was stirred for 11 hours at 70° C., poured into water and extracted with ether. The extract was washed with water, dried with potassium carbonate and evaporated. The residue was chromatographed on a column of 500 g of neutral aluminium oxide (activity II). Elution with benzene removed the less polar components and the desired base (7.17 g) was then eluted with a mixture of benzene and chloroform. The base was oily and by neutralization with maleic acid yielded 8.0 g of hydrogen maleate crystallizing from a mixture of acetone and ether and melted as a pure compound at 180°–181.5° C.

The starting α-(1-methyl-4-piperidyl)-2-(2,5-difluorophenylthio)-5-methoxybenzyl alcohol is a novel compound which may be prepared by the following procedure:

A mixture of 19.7 g of 2-bromo-5-methoxybenzaldehyde (of Example 9, reference above), 14.1 g of 2,5- difluorothiophenol (of Example 11, reference above), 14.0 g of potassium carbonate, 75 ml dimethylformamide and 2.1 g of copper catalyst is stirred and heated to 150° C. for 6 hours. It is then diluted with 150 ml of water and extracted with benzene. The extract is washed with water, dried with magnesium sulfate and evaporated. The residue is processed by distillation. There are obtained 13.3 g (52%) of 2-(2,5-difluorophenylthio)-5-methoxy-benzaldehyde boiling at 163°-165° C./40 Pa. The product is crystallized from cyclohexane and melts in a pure state at 67°-68° C.

A solution of a Grignard reagent is prepared by a reaction of 6.7 g of 4-chloro-1-methylpiperidine with 1.25 g of magnesium in 40 ml of tetrahydrofuran and is treated while stirring for 10 minutes with a solution of 9.35 g 2-(2,5-difluorophenylthio)-5-methoxy-benzaldehyde in 20 ml of tetrahydrofuran, added dropwise. The mixture is refluxed for 3 hours and, after cooling, it is decomposed with a 20% ammonium chloride solution and extracted with benzene. The extract is washed with water, dried with potassium carbonate and evaporated. There are obtained 12.6 g (100%) of crude oily α-(1-methyl-4-piperidyl)-2-(2,5-difluorophenylthio)-5-methoxybenzyl alcohol which is used in this state for the next reaction. For characterization the crystalline hydrogen oxalate may be prepared by neutralization of a sample with oxalic acid; it is purified by crystallization from acetone and melts at 160°-163° C.

EXAMPLE 13

2-Fluoro-8-(trifluoromethylthio)-6-(1-methyl-4-piperidyl)-6H-dibenz(b,e)-1,4-oxathiepin A solution of 26.9 g of crude α-(1-methyl-4-piperidyl)-2-(2,5-difluorophenylthio)-5-(trifluoromethylthio)benzyl alcohol in 100 ml of dimethylformamide was added to a suspension of 4.3 g of sodium hydride in 150 ml of dimethylformamide while stirring in a nitrogen atmosphere. The mixture was stirred for 15 hours at 70° C., then decomposed by pouring into water and extracted with ether. The extract was washed with water, dried with potassium carbonate and evaporated. The residue was chromatographed on a column of 1 kg of neutral aluminum oxide (activity II). After the elution of the less polar components with benzene, 5.3 g of the desired base was eluted with chloroform. It then crystallized from petroleum ether and melted at 77°-81° C. Neutralization with maleic acid yielded the hydrogen maleate which was purified by crystallization from a mixture of acetone and ether and melted at 151°-153° C.

The starting α-(1-methyl-4-piperidyl)-2-(2,5difluorophenylthio)-5-trifluoromethylthio)benzyl alcohol is a novel compound which is prepared by the following procedure.

A mixture of 106.2 g of 4-(trifluoromethylthio)-chlorobenzene (L.M. Jegupolskij and M.S. Marenec, Zh.Obshth. Khim. 29, 278, 1959) and 20 g of paraformaldehyde is stirred and treated at −5° C. with 61 g of chlorosulfonic acid, added dropwise. The mixture is stirred for 3 hours at a minimum temperature of 0° C. then for 12 hours at +5° C. and is decomposed by pouring on ice. The product is isolated by extraction with a mixture of benzene and chloroform. Then, the extract is dried with magnesium sulfate, evaporated and the residue distilled. As the first fraction with a b.p. of about 70° C./1.6 kPa there are recovered 58 g of unchanged starting compound. There are then obtained 26.8 g of a fraction boiling at 115°-140° C./2 kPa which represents a mixture of the monochloromethyl derivatives; according to evaluation with gas chromatography and with the $^1$H-NMR spectroscopy it contains 80% of the desired 2-chloromethyl-4-(trifluoromethylthio)chlorobenzene and 20% of undesired isomer. The redistilled sample has a b.p. of 118°-120° C./1.6 kPa. The substance is suitable for further processing in the crude state.

A mixture of 55.7 g of crude 2-chloromethyl-4-(trifluoromethylthio)chlorobenzene, 23 g of potassium acetate, 150 ml of dimethyl sulfoxide and 10 g of triethylbenzylammonium chloride is stirred for 5 hours at 60° C. It is decomposed by pouring into water, extracted with benzene and the benzene evaporated. The oily residue is dissolved in 200 ml of ethanol, 100 ml of water and 20 ml of hydrochloric acid are added and the mixture is stirred and refluxed for 7 hours. Ethanol is distilled off, the residue mixed with water and extracted with benzene. The oil obtained by evaporation of the dried extract, is distilled in vacuo. There are obtained 40.2 g crude 2-chloro-5-(trifluoromethylthio)benzyl alcohol boiling at 140°-150° C./2 kPa. According to the $^1$H-NMR spectrum the product contains approximately 80% of the named compound and the remainder is the position isomer. In this state the substance is suitable for further processing.

Triethylbenzylammonium chloride (3.6 g) is added to a solution of 39.9 g of crude 2-chloro-5-(trifluoromethylthio) benzyl alcohol in 400 ml of dichloromethane and the mixture is treated dropwise at 15°-20° C. with a solution of 20.6 g of potassium dichromate in 270 ml of water containing 135 ml of sulfuric acid. The mixture is stirred for 4 hours at room temperature and allowed to stand overnight. The aqueous layer is then separated and the organic layer washed with water and a 5% sodium hydroxide solution, dried with magnesium sulfate and evaporated. The residue is distilled in vacuo. There are obtained 34.1 g of crude 2-chloro-5-(trifluoromethylthio)benzaldehyde boiling at 120°-130° C./2 kPa. According to the $^1$H-NMR spectrum the product consists of approximately 80% of the named compound and the remainder is the position isomer. In this state the substance is suitable for further processing.

2,5-Difluorothiophenyl (of Example 11, reference given) (13.4 g) and a solution of 4.0 g of sodium hydroxide in 7 ml of water are added to a solution of 27.6 g of crude 2-chloro-5-(trifluoromethylthio)benzaldehyde in 30 ml of hexamethylphosphortriamide. Following the spontaneous reaction, the mixture is stirred for 5.5 hours at 100° C. and decomposed by pouring into water. Then, the separated crystalline substance is filtered with suction after standing for several hours, dried in vacua and recrystallized from cyclohexane. There are obtained 24.0 g of crude 2-(2,5-fluorophenylthio)-5-(trifluoromethylthio)benzaldehyde melting at 92°-102° C. The pure compound is obtained by further crystallization from cyclohexane, m.p. 103°-104.5° C.

A solution of a Grignard reagent is prepared by a reaction of 12.0 g of 4-chloro-1-methylpiperidine with 2.4 g of magnesium in 70 ml of tetrahydrofuran and is treated dropwise for 10 minutes with a solution of 21.2 g of 2-(2,5-difluorophenylthio)-5(trifluoromethylthio)-benzaldehyde in 40 ml of tetrahydrofuran. The mixture is refluxed for 5 hours and, after cooling, decomposed with a 20% ammonium chloride solution and extracted with benzene. The extract is washed with water, dried with potassium carbonate and evaporated. There are obtained 26.9 g of crude oily α-(1-methyl-4-piperidyl)-2-(2,5-difluorophenylthio)-5-(trifluoromethylthio)benzyl alcohol which is used in this state for further reaction.

EXAMPLE 14

11-(2-Dimethylaminoethyl)-11H-dibenzo(b,e)-1,4-dithiepin

A solution of 3.40 g of 11H-dibenzo(b,e)-1,4-dithiepin (K. Sindelar, M. Protiva and M. Hrubantova, Czech. 202.239) in 50 ml of ether was treated dropwise over 20 minutes of 15% n-butyllithium solution in hexane in a nitrogen atmosphere. The mixture was stirred for 30 minutes at room temperature and then treated with external cooling with ice and water and with 10 ml of 2-dimethylaminoethyl chloride, added dropwise. Then, the mixture was stirred for another 2 hours at room temperature. It was then washed with water and the basic product extracted into a mild excess of 1:1 dilute hydrochloric acid. The acid aqueous layer was separated, made alkaline with aqueous ammonia and the base extracted with ether. The extract was dried with potassium carbonate and evaporated. The remaining oily base was dissolved in 7 ml of acetone and treated with a solution of 1.81 g of oxalic acid in 5 ml of acetone. The crystalline hydrogen oxalate (5.31 g) separated, was filtered with suction and purified by recrystallization from aqueous ethanol, m.p. 195°–197° C.

EXAMPLE 15

11-(3-Dimethylaminopropyl)-11H-dibenzo(b,e)-1,4-dithiepin

A solution of 3.10 g 11H-dibenzo(b,e)-1,4-dithiepin (of example 14, reference given) in 50 ml of ether was stirred and treated dropwise with 10 ml of 15% n-butyllithium solution in hexane for 15 minutes in a nitrogen atmosphere. The mixture was stirred for another 30 minutes at room temperature. It was then treated dropwise with 10 ml of 3-dimethylaminopropyl chloride, the mixture stirred for 4 hours and washed with water. The basic product was then extracted with dilute hydrochloric acid, the acid layer made alkaline with aqueous ammonia and the base extracted with ether. Processing of the extract yielded 3.7 g for oily base which was chromatographed on a column of 200 g neutral of aluminium oxide (activity II). A small amount of less polar impurities was initially eluted with benzene which then eluted 2.89 g of a homogeneous oily base which was converted by neutralization with oxalic acid to the hydrogen oxalate, m.p. 181°–182° C. (ethanol).

EXAMPLE 16

11-(2-Dimethylaminoethyl)-11H-dibenz(b,f)-1,4-oxathiepin

A solution of 10.1 g of 11H-dibenz(b,f)-1,4-oxathiepin (K. Sindelar, M. Protiva and M. Hrubantova, Czech. 202.238) in 120 ml of ether was stirred and treated dropwise over 30 minutes with 30 ml of a 15% n-butyllithium solution in hexane in a nitrogen atmosphere. The mixture was stirred for another 30minutes at room temperature and 30 ml of 2-dimethylaminoethyl chloride were added and the mixture stirred for an additional 5 hours. After 24 hours standing, it was washed with water and the basic product extracted with dilute hydrochloride acid. The acid aqueous solution was separated, made alkaline with aqueous ammonia and the base isolated by extraction with benzene. The extract was dried with potassium carbonate and evaporated. 11.5 g (86%) of crude oily product (base) was obtained and neutralized with 5.4 g of oxalic acid in acetone. There were obtained 15.2 g of crude hydrogen oxalate melting at 186°–186.5° C. which was recrystallized from a mixture of ethanol and ether, m.p. 187.5°–189.5° C.

EXAMPLE 17

11-(3-Dimethylaminopropyl)-11H-dibenz(b,f)-1,4-oxathiepin

A solution of 10.1 g of 11H-dibenz(b,f)-1,4-oxathiepin (of Example 16, reference given) in 120 ml of ether was stirred in a nitrogen atmosphere and treated dropwise for 15 minutes at 5° C. with 30 ml of 15% n-butyllithium in hexane. The mixture was stirred for another 30 minutes, treated with 30 ml of 3-dimethylaminopropyl chloride and stirred for 5 hours at room temperature. After standing overnight it was washed with water and the basic product extracted with dilute hydrochloride acid. The acid aqueous extract was made alkaline with aqueous ammonia and the base extracted with benzene. The extract was then dried with potassium carbonate and evaporated. There were obtained 12.6 g (89%) of a crude oily base which was neutralized with 5.3 g of oxalic acid in acetone. Addition of ether lead to precipitation of 16.1 g of crude hydrogen oxalate, m.p. 118°–122° C. Crystallization from a mixture of 95% ethanol and ether afforded the pure hydrogen oxalate hemihydrate with a m.p. of 118°–121° C.

EXAMPLE 18

2-Chloro-11-(3-dimethylaminopropyl)-11H-dibenz(b,f)-1,4-oxathiepin

A solution of 6.0 g of 2-chloro-11H-dibenz(b,f)-1,4-oxathiepin in 100 ml of ether was stirred in a nitrogen atmosphere and treated dropwise for 15 minutes with 18 ml of 15% n-butyllithium in hexane. The mixture was stirred for 45 minutes at room temperature, treated with 20 ml of 3-dimethylaminopropyl chloride and stirred for 7 hours. After standing overnight, it was washed with water and the base extracted with dilute hydrochloride acid. The aqueous extract was separated, made alkaline with a 20% sodium hydroxide solution and the base extracted with ether. The extract was then dried with potassium carbonate and evaporated. There were obtained 6.43 g of an inhomogeneous oil which was chromatographed on a column of 450 g of neutral aluminium oxide (activity II). Elution with benzene and then with chloroform yielded 4.8 g of a homogeneous oily base which was neutralized with oxalic acid in acetone to give the hydrogen oxalate crystallizing from a mixture of acetone and ethanol and melting at 167°–168° C.

The starting 2-chloro-11H-dibenz(b,f)-1,4-oxathiepin is a novel compound which may be prepared by the following procedure:

A solution of 120 g of 5-chloro-2- iodobenzoic acid (K. Pelz et al., Collect.Czech.Chem.Commun. 33, 1852, 1968) in 145 ml of tetrahydrofuran is stirred and treated at 10°–20° C. for 45 minutes with 16.1 g of sodium borohydride. The mixture is then stirred for 30 minutes at this temperature and treated with a solution of 80.3 g (71.4 ml) of boron trifluoride etherate in 40 ml of tetrahydrofuran. It is stirred for another 3 hours and while cooling with ice-cold water it is decomposed at a maximum temperature of 8° C. with 50 ml of 5% hydrochloric acid added dropwise. It is diluted with water and extracted with benzene. The extract is washed with a 5% sodium hydroxide solution and water, dried with magnesium sulfate and evaporated. There are obtained 100 g (96%) of crude 5-chloro-2-iodobenzyl alcohol with m.p. of 115°–117° C. The analytically pure substance is obtained by crystallization from ethanol; m.p. 116°–117° C.

A mixture of 41.6 g of phosphorus tribromide, 25 ml of benzene and 8.2 ml of pyridine is prepared while cooling and while stirring it is treated dropwise at a maximum temperature of 10° C. with 108.3 g of 5-chloro-2-iodobenzyl alcohol. Then, it is stirred for 4 hours at room temperature and for 1 hour at 50° C. After cooling, it is diluted with 120 ml of chloroform, the mixture washed with 25 ml of 5% hydrochloric acid, a 5% sodium hydroxide solution and with water, dried with magnesium sulfate and evaporated. There are obtained 126 g (95%) of crude 5-chloro-2-iodobenzyl bromide melting at 75°–79° C. The pure product is obtained by crystallization from a mixture of benzene and petroleum ether, m.p. 77°–79° C.

A solution of 125.6 g of 5-chloro-2-iodobenzyl bromide in 500 ml of dimethylformamide is added to a mixture of 640 ml of dimethylformamide, 52.4 g of potassium carbonate and 47.8 g of 2-hydroxythiophenol (R. Leuckart, J.Prakt.Chem. /2/ 41, 192, 1890). Then, the mixture is stirred for 1 hour at room temperature, treated with 57 g. of potassium carbonate and 4.5 g of copper and is refluxed for 6 hours. Dimethylformamide is distilled off under reduced pressure, the residue diluted with water and shaken with benzene. After filtration, the benzene layer is separated, washed with water, dried with potassium carbonate and evaporated. By distillation of the residue there are obtained 42.5 g (45%) of 2-chloro-11H-dibenz(b,f)-1,4-oxathiepin with a b.p. of 148°–168° C./85 Pa and m.p. of 66.76° C. The pure product is obtained by crystallization from methanol and melts at 78°–79° C.

EXAMPLE 19

2-Chloro-11-(2-dimethylaminoethyl)-11H-dibenz (b,f)-1,4-oxathiepin 10,10-dioxide A solution of 4.0 g of 2-chloro-11H-dibenz(b,f)-1,4-oxathiepin 10,10-dioxide in 40 ml of dimethylformamide was treated with 0.63 g of sodium hydride and the mixture stirred for 30minutes at 70° C. Next, 11 ml of 2-dimethylaminoethyl chloride were added and the mixture stirred for another 3.5 hours at 70° C. Ethanol (4 ml) was added dropwise followed by 500 ml of water and the mixture extracted with benzene. From the benzene solution, the base was extracted with 100 ml of 3M-HCl, the acid solution separated and made alkaline with aqueous ammonia. The released base was extracted with chloroform, the extract dried with potassium carbonate and evaporated. There were obtained 2.65 g of an oily base. The hydrochloride was obtained by neutralization with hydrogen chloride in ether; it was purified by crystallization from ethanol and melted at 235°–237° C.

The starting 2-chloro-11H-dibenz(b,f)-1,4-oxathiepin 10, 10-dioxide is a novel compound which is prepared in the following manner:

A stirred solution of 10.0 g of 2-chloro-11H-dibenz (b,f)-1,4-oxathiepin (cf. Example 18) in 100 ml of acetic acid is treated dropwise with 12 ml of 30% hydrogen peroxide and the mixture refluxed for 30 minutes. After cooling, it is poured into 500 ml of water and extracted with chloroform. The extract is dried with magnesium sulfate and evaporated. There are obtained 11.1 g (98%) of crude 2-chloro-11H-dibenz (b,f)-1,4-oxathiepin 10,10-dioxide melting at 159°–166° C. The pure substance melting at 166.5°–167.5° C. is obtained by crystallization from ethanol.

Example 20

2-Chloro-11-(3-piperidinopropyl)-11H-dibenz (b,f)-1,4-oxathiepin 10,10-Dioxide

A solution of 4.18 g 2-chloro-11H-dibenz (b,f)-1,4-oxathiepin 10,10-dioxide in 40 ml of dimethylformamide was treated with 0.65 g of sodium hydride and the mixture stirred for 4.5 hours at 70° C. Thereafter, 10 ml of 3-piperidinopropyl chloride were added and the mixture stirred for 3.5 hours at 70° C. It was then decomposed by dropwise addition of 4 ml of ethanol and diluted with 700 ml of water and extracted with benzene. From the benzene solution the base was extracted with 100 ml of 3M-HCl. The separated acid aqueous solution was made alkaline with aqueous ammonia and the base extracted with chloroform. The extract was dried with potassium carbonate and evaporated. The residue was chromatographed on a column of 400 g of neutral aluminum oxide (activity II). The less polar impurities were eluted with benzene and 4.37 g of homogeneous oily base were eluted with benzene and 4.37 g of homogeneous oily base were eluted with chloroform. Neutralization with hydrogen chloride in a mixture of ethanol and ether yielded the hydrochloride. By crystallization from a mixture of ethanol and ether the pure product was obtained, m.p. 177°–179° C.

Example 21

2-Chloro-11-(1-methyl-4-piperidyl )-11H-dibenz(b,f)-1,4-oxathiepin

A stirred solution of 6.45 g of 2-chloro-11H-dibenz (b,f)-1,4-oxathiepin (cf.Example 18) in 100 ml tetrachloromethane was treated for 4.5 hours at 60° C. with a solution of 3.54 g of sulfuryl chloride in 100 ml of tetrachloromethane, added dropwise. The mixture was stirred for another 1 hour at 60° C., tetrachloromethane evaporated, the residue dissolved in 20 ml benzene and the solution of a Grignard reagent. The reagent was prepared by reaction of 7.0 g of 4-chloro-1-methylpiperidine with 1.3 g of magnesium in 45 ml of tetrahydrofuran. The mixture was refluxed for 3.5 hours and, after cooling, it was decomposed with a 20% ammonium chloride solution and extracted with benzene. The extract was washed with water and the basic product reextracted by shaking with excessive dilute hydrochloric acid. The acid solution was made alkaline with aqueous ammonia and the base isolated by extraction with ether. After drying the extract with potassium carbonate, benzene was evaporated. The residue (3.7 g) was chromatographed on a column of 400 g of neutral aluminium oxide (activity II). Elution with benzene separated a less polar substance and 1.47 g desired base were eluted with a mixture of benzene and chloroform. The base was oily and was neutralized with maleic acid in a mixture of acetone and ether to yield 1.73 g of hydrogen maleate. The pure compound with a m.p. of 184°–186.5° C. was obtained by crystallization from the noted mixture of solvents.

Example 22

2-Chloro-11-(1-methyl-4-piperidyl)-11H-dibenz(b,f)-1,4-oxathiepin

A solution of 7.05 g of 2-chloro-11H-dibenz (b,f)-1,4-oxathiepin (cf. Example 18) in 30 ml of benzene was treated with 3.85 g of N-chloro-succinimide. The mixture was stirred for 5hours while maintaining a maximum temperature of 25° C. by external cooling. After standing overnight, the mixture was added dropwise to a solution of a Grignard reagent prepared by reaction of 7.0 g of 4-chloro-1-methylpiperidine with 1.3 g of magnesium in 40 ml of tetrahydrofuran at 20°–25° C. The mixture was stirred for another 5 hours at room temperature, allowed to stand for 48 hours and decomposed with a 20% ammonium chloride solution. It was extracted with benzene, the extract washed with water and the basic product reextracted by shaking with excessive dilute hydrochloric acid. The acid aqueous solution was made alkaline with aqueous ammonia and the base isolated by extraction with benzene. After drying with potassium carbonate, the extract was evaporated and the remaining oil (6.4 g) chromatographed on a column of 400 g of neutral aluminium oxide (activity II). Elution with benzene separated a small amount of a less polar impurity and a mixture of benzene and chloroform then eluted 4.16 g of the desired homogeneous base. Neutralization with maleic acid yielded the hydrogen maleate, m.p. 183.5°–186.5° C., which was identical to the product described in the preceding Example.

Example 23

2-Trifluoromethyl-11-(1-methyl-4-piperidyl)-11H-dibenz (b,f)-1,4-oxathiepin

A solution of 7.4 g of 2-trifluoromethyl-11H-dibenz (b,f)-1,4-oxathiepin in 100 ml of tetrachloromethane was stirred and treated for 4 hours at 60° C. with a solution of 3.54 g of sulfuryl chloride in 100 ml of tetrachloromethane, added dropwise. The mixture was stirred for another 1.5 hours at 60° C., allowed to stand overnight and tetrachloromethane evaporated under reduced pressure. The residue was dissolved in 20 ml of tetrahydrofuran and the solution added dropwise over 15 min to a solution of a Grignard reagent prepared by reaction of 7.0 g 4-chloro-1-methylpiperidine with 1.3 g magnesium in 30 ml of tetrahydrofuran. The mixture was refluxed for 8 hours and, after standing overnight, it decomposed with a 20% ammonium chloride solution. It was extracted with ether, the extract washed with water and the basic product reextracted by shaking with excessive dilute hydrochloric acid. The acid aqueous solution was made alkaline with aqueous ammonia and the base isolated by extraction with benzene. The extract was dried with potassium carbonate and evaporated. The residue (5.0 g) was chromatographed on a column of 200 g of neutral aluminium oxide (activity II). Benzene eluted a small quantity of a less polar component and 1.8 g of a homogeneous desired base were then eluted with a mixture of benzene and chloroform. Neutralization with oxalic acid in acetone yielded the hydrogen oxalate crystallizing as a hemihydrate, m.p. 193°–197° C. with decomposition (aqueous acetone).

The starting 2-trifluoromethyl-11H-dibenz (b,f)-1,4-oxathiepin is a novel compound which may be obtained by the following procedure:

A solution of 45 g of 2-chloro-5-trifluoromethylbenzyl chloride (B. Pecherer, U.S. Pat. No. 3,465,051; Chem.Abstr. 71, 123 885, 1969) and 37.6 g of 2-hydroxythiophenol (cf.Example 18, reference given) in 800 ml of dimethylformamide is treated with 27.2 g of potassium carbonate and the mixture stirred for 3 hours in a nitrogen atmosphere at a room temperature. Further 30 g of potassium carbonate and 3 g of copper are then added and the mixture refluxed for 12 hours. Dimethylformamide is distilled off in vacuo and the residue separated between water and benzene. It is then filtered, the benzene layer of the filtrate separated, dried with potassium carbonate and processed by distillation. There are obtained 40.2 g of (73%) 2-trifluoromethyl-11H-dibenz (b,f)-1,4-oxathiepin boiling at 135°–137° C./0.1 kPa. The distillate crystallizes from petroleum ether and the pure 1,4-oxathiepin (cf. Example 16) in 30 ml of benzene was added dropwise for 1 hour to a refluxing solution of 3.9 g of ethyl chloroformate in 15 ml of benzene. The mixture was refluxed for 1.5 hours and, after cooling washed with water, with 10% sulfuric acid and again with water. It was then dried with magnesium sulfate and evaporated. The residue (the crude carbamate) was dissolved in 10 ml of ethanol and the solution treated with 9.0 g of potassium hydroxide. Then, the mixture was refluxed for 2 hours in a bath having a temperature of 130° C. It was diluted with water and extracted with benzene. From the benzene solution the basic product was reextracted by shaking with excessive 10% hydrochloric acid. The aqueous layer together with the oily hydrochloride were separated, made alkaline with aqueous ammonia and the released base extracted with benzene. The extract was dried with potassium carbonate and evaporated. There were obtained 4.0 g of an oily base which was neutralized with 1.9 g of oxalic acid in acetone. The hydrogen oxalate crystallized in a yield of 5.15 g was recrystallized from aqueous ethanol and melted at 210°–211° C.

Example 25

11-(3-Methylaminopropyl)-11H-dibenz(b,f)-1,4-oxathiepin

A solution of 8.2 g of 11-(3-dimethylmaninopropyl)-11H-dibenz(b,f)-1,4-oxathiepin (cf. Example 17) in 30 ml of benzene was added dropwise for 1 hour to a refluxing solution of 3.86 g of ethyl chloroformate in 15 ml of benzene. The mixture was refluxed for 1.5 hours and, after cooling, it was washed with water, 10% sulfuric acid and water, dried with magnesium sulfate and evaporated. The residue (the carbamate) was dissolved in 10 ml of ethanol, the solution treated with 9.0 g of potassium hydroxide and the mixture refluxed for 2 hours in a bath having a temperature of 140° C. It was then diluted with water and extracted with benzene. From the benzene solution, the base was reextracted by shaking with excessive 10% hydrochloric acid. The acid aqueous layer with the oily hydrochloride were separated, made alkaline with aqueous ammonia and the released base extracted with benzene. The extract was dried with potassium carbonate and evaporated. There were obtained 6.1 g (79%) of an oily base. It was dissolved in acetone and the solution neutralized with 2.8 g of oxalic acid in acetone. Upon standing, 7.7 g of the hydrogen oxalate crystallized and the product recrystallized from ethanol with a melting point of 161°–162° C.

Example 26

8-Methoxy-6-(4-piperidyl)-6H-dibenz(b,e)-1,4-oxathiepin

A stirred solution of 13.1 g of 8-methoxy-6-(1-methyl-4-piperidyl)-6H-dibenz(b,e)-1,4-oxathiepin (cf. Example 9) in 50 ml of benzene was treated dropwise for 1.5 hours with a solution of 6.5 g of ethyl chloroformate in 30 ml of benzene and the mixture refluxed for 1.5 hours. After cooling, it was washed with water, 10% sulfuric acid, 5% sodium hydrogen carbonate solution, dried with magnesium sulfate and evaporated. The residue (the carbamate) was dissolved in 17 ml of ethanol, the solution treated with 15 g of potassium hydroxide and the mixture refluxed for 2 hours in a bath with a temperature of 140° C. It was then diluted with water and extracted with benzene. From the benzene solution, the base extracted into excessive 10% hydrochloric acid, the acid extract made alkaline with aqueous ammonia and the released base extracted with benzene. The extract was dried with potassium carbonate and evaporated. There were obtained 11.1 g (88%) of an oily base which was neutralized with oxalic acid in acetone and yielded the hemioxalate, i.e. the neutral oxalate, crystallizing as a hemihydrate, m.p. 234°–235.5° C. (95% ethanol).

Example 27

2-Fluoro-8-chloro-6-(4-piperidyl)-6H-dibenz(b,e)-1,4-oxathiepin

A boiling solution of 11.0 g of 2-fluoro-8-chloro-6-(1-methyl-4-piperidyl)-6H-dibenz(b,e)-1,4-oxathiepin (cf. Example 11) in 50 ml benzene was treated dropwise for 30 minutes with a solution of 5.7 ml of ethyl chloroformate in 30 ml of benzene and the mixture refluxed for 1.5 hours. After cooling, a small quantity of the hydrochloride (monohydrate) of the starting compound was filtered off, the filtrate washed with water, 10% sulfuric acid and with a 5% sodium hydrogen carbonate solution. Then, it was dried with magnesium sulfate and evaporated. The residue (the carbamate) was dissolved in 15 ml of ethanol, the solution treated with 13 g of potassium hydroxide and the mixture refluxed for 2 hours (bath of 125° C.) After cooling, it was diluted with water and extracted with benzene. From the benzene solution, the base was extracted with excessive 10% hydrochloric acid, the precipitated hydrochloride filtered by suction, suspended in the acid aqueous layer of the filtrate and the suspension made alkaline with aqueous ammonia. The free base was next extracted with benzene, the extract dried with potassium carbonate and evaporated. There were obtained 9.0 g of crystalline base which crystallized from cyclohexane and melted at 120°–122° C. Neutralization with hydrogen chloride yielded the hydrochloride crystallizing from aqueous ethanol and melting in the pure state at 313°–317° C. with decomposition.

EXAMPLE 28

8-Methoxy-6-/1-(2-hydroxyethyl)-4-piperidyl/6H-dibenz(b,e)-1,4-oxathiepin

A mixture of 5.05 g of 8-methoxy-6-(4-piperidyl)-8H-dibenz(b,e)-1,4-oxathiepin (cf. Example 27), 5.8 g of 2-bromoethanol, 5.0 g of potassium carbonate and 100 ml of acetone was refluxed for 8 hours. After cooling, the undissolved components were filtered off and the filtrate evaporated. The residue was chromatographed on a column of 400 g of neutral aluminium oxide (activity II). Elution with a mixture of benzene and chloroform removed the less polar components and 2.16 g of a homogeneous oily base were then eluted with chloroform. It was neutralized with fumaric acid in ether and yielded the hydrogen fumarate melting at 101°–104° C.

Example 29

2-Fluoro-8-chloro-6-/1-(2-hydroxyethyl)-4-piperidyl/-6H-dibenz(b,e)-1,4-oxathiepin A mixture of 7.0 g of 2-fluoro-8-chloro-6(4-piperidyl)-6H-dibenz(b,e)-1,4-oxathiepin (cf. Example 27), 3.75 g 2-bromoethanol, 5.0 g of potassium carbonate and 100 ml of acetone was stirred and refluxed for 6 hours. After cooling, the precipitated solid was filtered off, washed with acetone and the filtrate evaporated. The residue was dissolved in ether, a small amount of an insoluble substance was filtered off and the filtrate neutralized with 2.0 g of oxalic acid in acetone. 5.55 g of hydrogen oxalate crystallizes and was purified by crystallization from acetone, m.p. 141°–143° C.

EXAMPLE 30

8-Methoxy-6-/1-(4-hydroxypentyl)-4-piperidyl/-6H-dibenz(b,e)-1,4-oxathiepin

A solution of 5.90 g of 8-methoxy-6-/1-(4-oxopentyl)-4-piperidyl/-6H-dibenz(b,e)-1,4-oxathiepin in 100 ml of ethanol was treated with 1.0 g of sodium borohydride in 5 ml of water containing 1 drop of a 20% sodium hydroxide solution, and the mixture refluxed for 3 hours while stirring. It was then diluted with 10 ml of acetone, stirred for 30 minutes, evaporated under reduced pressure and the residue separated between a dilute sodium hydroxide solution and benzene. The benzene layer was evaporated and neutralized with 2.0 g of maleic acid in a mixture of acetone and ether. The separated oily maleate was isolated by decantation and washed with ether. There it was decomposed with aqueous ammonia and extracted with ether yielding 5.6 g of an oily base. Neutralization with a solution of fumaric acid in ether yielded crystalline hydrogen fumarate melting at 95°–99° C.

The starting compound 8-methoxy-6-/1-(4-oxopentyl)-4-piperidyl/-6H-dibenz(b,e)-1,4-oxathiepin is a novel compound which is obtained by the following procedure:

Potassium carbonate (5.0 g) is added to a solution of 5.65 g of 8-methoxy-6-(4-piperidyl)-6H-dibenz(b,e)-1,4-oxathiepin (cf. Example 26) and 3.9 g 5-bromopentan-2-one (A. Lipp, Ber.Deut.Chem. Ges. 22, 1196, 1889) in 100 ml of acetone and the mixture is refluxed for 7 hours with stirring. After cooling, it is filtered and the filtrate is evaporated. The residue is dissolved in acetone, neutralized with maleic acid and the oily maleate is separated by addition of ether. It is then isolated by decantation and washed with ether. By decomposition with a dilute sodium hydroxide solution, the base is released again and is isolated by extraction with ether. Processing of the extract yields 7.0 g of an oily base of 8-methoxy-6-/1-(4-oxopentyl)-4-piperidyl/-6H-dibenz(b,e)-1,4-oxathiepin which is neutralized with oxalic acid in a mixture of acetone and ether and yields the crystalline oxalate melting at 87°–89° C. (acetone-ethanol).

EXAMPLE 31

2-Fluoro-8-chloro-6-/1-(2-decanoyloxyethyl)-4-piperidyl/-6H-dibenz(b,e)-1,4-oxathiepin From a mixture of 4.35 g of 2-fluoro-8-chloro-6-/1-(2-hydroxyethyl)-4-piperidyl/-6H-dibenz(b,e)-1,4-oxathiepin (cf. Example 29), 6.0 g of decanoic acid and 50 ml of xylene, the wet xylene was slowly distilled off and was substituted by dry xylene. Over 6 hours there were distilled some 350 ml of wet xylene and the mixture treated with the same quantity of anhydrous xylene. The residue was diluted with benzene, the solution washed with a 5% sodium hydroxide solution and water, dried with potassium carbonate and evaporated. The residue was chromatographed on a column of 150 g of neutral aluminium oxide (activity II). Elution with benzene first removed a small amount of a less polar impurity and the same solvent then eluted 3.35 g of the homogeneous ester base. Neutralization of a sample with maleic acid in a mixture of acetone and ether resisted in the formation of a crystalline hydrogen maleate melting at 135°–136.5° C. (acetone-ether).

EXAMPLE 32

2-Chloro-11-(1-methyl-4-hydroxy-4-piperidyl)-11H-dibenz(b,f)-1,4-oxathiepin

A solution of 9.9 g of 2-chloro-11H-dibenz(b,f)-1,4-oxathiepin (cf. Example 18) in 130 ml of ether was stirred in a nitrogen atmosphere and treated dropwise for 10 minutes at 10° C. with 30 ml of a 15% n-butyllithium solution in hexane. The mixture was stirred for 1 hour and then treated dropwise for 10 minutes with a solution of 7.2 g of 1-methyl-4-piperidone in 20 ml of ether. The mixture was stirred for 5 hours at room temperature, allowed to stand overnight, washed with water, dried with potassium carbonate and evaporated. The remaining crude oily base was dissolved in ether and the solution neutralized with 4.5 g of maleic acid in ethanol. There were obtained 10.8 g of crystalline hydrogen maleate which melted in pure state at 195.5°–197° C. (ethanol).

EXAMPLE 33

11-(Dimethylaminomethyl)-11H-dibenz(b,f)-1,4-oxathiepin

A solution of 2.60 g of 11H-dibenz(b,f)-1,4-oxathiepin-11-carboxylic acid dimethylamide in 40 ml of tetrahydrofuran was treated with 1.9 g of sodium borohydride and then while stirring in a nitrogen atmosphere and under external cooling with ice it was treated dropwise for 45 minutes with 6 ml of boron trifluoride eherate. The mixture was refluxed for 3 hours and evaporated. The residue was then dissolved in 50 ml of ethanol, 25 ml of a 20% sodium hydroxide solution were added and the mixture refluxed for 6 hours. Ethanol was then evaporated, the residue diluted with water and extracted with benzene. The resultant oily base was dissolved in ethanol and the solution neutralized with 1.3 g of oxalic acid. By standing, there crystallized 2.45 g of hydrogen oxalate, crystallizing from a mixture of acetone, ethanol and ether and melting at 179.5°–180.5° C.

The starting dimethylamide of 11H-dibenz(b,f)-1,4-oxathiepin-11-carboxylic acid is a novel compound which is obtained by the following procedure:

A mixture of 2.5 g of 11H-dibenz(b,f)-1,4-oxathiepin-11-carboxylic acid (K. Sindelar and M. Protiva, Czech.202.241), 10 ml of benzene and 5 ml of thionyl chloride is refluxed for 2.5 hours. The volatile components are then evaporated, the remaining crude acid chloride dissolved in 20 ml of benzene and the resultant solution added dropwise for 5 minutes to a stirred solution of 15 g of dimethylamine in 50 ml of benzene, which is cooled with ice from outside. The mixture is stirred for 4 hours, allowed to stand overnight at room temperature, washed with water, dried with magnesium sulfate and evaporated. There are obtained 2.65 g (96%) of crystalline dimethylamide of 11H-dibenz(b,f)-1,4-oxathiepin-11-carboxylic acid, which is purified by crystallization from a mixture of benzene and petroleum ether and melts at 144.5°–146° C.

EXAMPLE 34

8-Chloro-6-(1-methyl-4-piperidyl)-6H-dibenz(b,e)-1,4-oxathiepin 11-Oxide

8-Chloro-6-(1-methyl-4-piperidyl)-6H-dibenz(b,e)-1,4-oxathiepin (cf. Example 6)(2.18 g) was dissolved in a solution of 0.8 g of methanesulfonic acid in 25 ml of water. Next, 36 ml of a 30% hydrogen peroxide solution were added and the mixture allowed to stand at room temperature for 36 hours. It was then made alkaline with aqueous ammonia and extracted with benzene. The extract was dried with potassium carbonate and evaporated. By neutralization of the crude base (2.23 g) with oxalic acid in a mixture of acetone and ether there were obtained 2.6 g of hemioxalate (neutral oxalate) which crystallized from a mixture of aqueous ethanol and ether as a solvate with one molecule of ethanol, m.p. 150°–154° C. (a residue at 160° C.)

EXAMPLE 35

8-Chloro-6-(1-methyl-4-piperidyl)-6H-dibenz(b,e)-1,4-oxathiepin N-Oxide

A solution of 2.24 g of 8-chloro-6-(1-methyl-4-piperidyl)-6H-dibenz(b,e)-1,4-oxathiepin (cf. Example 6) in 15 ml of ethanol was treated with 1.5 ml of 28% hydrogen peroxide, the mixture stirred for 4 hours at 0° C. and allowed to stand for 3 days at room temperature. After an additional 12 hours standing at 0° C., the precipitated product was filtered with suction; 1.5 g, m.p. 126°–129° C. (residue at 140° C.)(ethanol).

What is claimed is:

1. Tricyclic compound of the formula

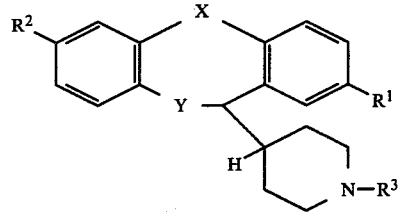

wherein
(a) X and Y are selected from the group consisting of oxygen and sulfur,
(b) $R^1$ is selected from the group consisting of hydrogen, a halogen atom, an alkyl, alkoxy or alkylthio group of 1–3 carbon atoms, a trifluoromethyl group, and a trifluoromethylthio group,
(c) $R^2$ is selected from the group consisting of hydrogen and fluorine atoms, and (d) $R^3$ is selected from the group consisting of hydrogen and a methyl group.

2. 2-Chloro-11-(1-methyl-4-piperidyl)-11H-dibenz(b,f)-1,4-oxathiepin and its salts.

3. 2-Trifluoromethyl-11-(1-methyl-4-piperidyl)-11H-dibenz-(b,f)-1,4-oxathiepin and its salts.

4. 6-(1-Methyl-4-piperidyl)-6H-dibenz(b,e)-1,4-oxathiepin and its salts.

5. 8-Chloro-6-(1-methyl-4-piperidyl)-6H-dibenz(b,e)-1,4-oxathiepin and its salts.

6. 8-Methoxy-6-(1-methyl-4-piperidyl)-6H-dibenz(b,e)-1,4-oxathiepin and its salts.

7. 8-Trifluoromethyl-6-(1-methyl-4-piperidyl)-6H-dibenz(b,e)-1,4-oxathiepin and its salts.

8. 8-Methoxy-6-/1-(2-hydroxyethyl)-4-piperidyl/-6H-dibenz(b,e)-1,4-oxathiepin and its salts.

9. 2-Fluoro-8-chloro-6-(1-methyl-4-piperidyl)-6H-dibenz(b,e)-1,4-oxathiepin and its salts.

10. 2-Fluoro-8-methoxy-6-(1-methyl-4-piperidyl)-6H-dibenz(b,e)-1,4-oxathiepin and its salts.

11. 2-Fluoro-8-(trifluoromethylthio)-6-(1-methyl-4-piperidyl)-6H-dibenz(b,e)-1,4-oxathiepin and its salts.

12. 2-Fluoro-8-chloro-6-(1-/2-decanoloxyethyl/-4-piperidyl)-6-dibenz(b,e)-1,4-oxathiepin.

* * * * *